United States Patent
Nishimori et al.

(10) Patent No.: US 10,001,469 B2
(45) Date of Patent: Jun. 19, 2018

(54) USE OF GPR83 TO IDENTIFY PRURITUS-RELATED SUBSTANCES

(71) Applicant: University of Miyazaki, Miyazaki (JP)

(72) Inventors: Toshikazu Nishimori, Miyazaki (JP); Rumi Nakayama, Miyazaki (JP)

(73) Assignee: University of Miyazaki, Miyazaki (JP)

( * ) Notice: Subject to any disclaimer, the term of this patent is extended or adjusted under 35 U.S.C. 154(b) by 10 days.

(21) Appl. No.: 14/823,378

(22) Filed: Aug. 11, 2015

(65) Prior Publication Data

US 2016/0033478 A1 Feb. 4, 2016

Related U.S. Application Data

(62) Division of application No. 13/819,142, filed as application No. PCT/JP2011/069178 on Aug. 25, 2011, now abandoned.

(60) Provisional application No. 61/471,338, filed on Apr. 4, 2011.

(30) Foreign Application Priority Data

Aug. 27, 2010 (JP) ................. 2010-191039

(51) Int. Cl.
| | |
|---|---|
| *A61K 49/14* | (2006.01) |
| *A61K 38/00* | (2006.01) |
| *A61K 39/00* | (2006.01) |
| *G01N 33/50* | (2006.01) |
| *C07K 14/52* | (2006.01) |
| *C07K 14/715* | (2006.01) |
| *C12N 15/113* | (2010.01) |
| *C07K 14/705* | (2006.01) |
| *C07K 7/06* | (2006.01) |
| *A61K 38/08* | (2006.01) |
| *A61K 49/00* | (2006.01) |

(52) U.S. Cl.
CPC ......... *G01N 33/5008* (2013.01); *A61K 38/08* (2013.01); *A61K 49/0008* (2013.01); *C07K 7/06* (2013.01); *C07K 14/52* (2013.01); *C07K 14/705* (2013.01); *C07K 14/715* (2013.01); *C12N 15/1138* (2013.01); *A61K 38/00* (2013.01); *C12N 2310/14* (2013.01); *G01N 2500/04* (2013.01); *G01N 2800/2842* (2013.01); *G01N 2800/7095* (2013.01)

(58) Field of Classification Search
None
See application file for complete search history.

(56) References Cited

U.S. PATENT DOCUMENTS

| | | |
|---|---|---|
| 2003/0165541 A1 | 9/2003 | Donovan |
| 2008/0274124 A1 | 11/2008 | Hannedouche et al. |

FOREIGN PATENT DOCUMENTS

| | | |
|---|---|---|
| EP | 1867994 | 12/2007 |
| JP | 20066311852 | 11/2006 |
| WO | WO 94/01548 | 1/1994 |
| WO | WO 2006/017688 | 2/2006 |

OTHER PUBLICATIONS

Supplementary European Search Report dated Jan. 12, 2015, based on foreign counterpart: European Application No. EP11819989.
Naono, Rumi, et al., "Intrathecal Administration of siRNA Induces Knock-Down of the Neurokinin 1 Receptor", Pain Research, vol. 23, No. 2, Jul. 19, 2008, pp. 106-107 with English Translation.
Naono, R., et al., "Pharmacological Characterization of Desensitization in Scratching Behaviour Induced by Intrathecal Administration of Hemokinin-1 in the Rat", Neuropeptides, vol. 42, 2008, pp. 47-55.
Sakurada, Chikai, et al., "Major Metabolites of Substance P Degraded by Spinal Synaptic Membranes Antagonize the Behavioral Response to Substance P in Rats", Journal of Pharmaceutical Sciences, vol. 88, No. 11, Nov. 1999, pp. 1127-1132.

*Primary Examiner* — Christine J Saoud
*Assistant Examiner* — Jon M Lockard
(74) *Attorney, Agent, or Firm* — McCarter & English, LLP

(57) ABSTRACT

The present invention provides a peptide having antagonist activity against SP, pain control activity, anti-inflammation activity, and anti-pruritic activity. The present invention further provides a method for searching for a therapeutic agent for pain, a therapeutic agent for inflammation, and a therapeutic agent for pruritus using G protein coupled receptor (GPR) 83, which is an HK-1 specific receptor.

4 Claims, 16 Drawing Sheets

USE OF GPR83 TO IDENTIFY PRURITUS-RELATED SUBSTANCES

CROSS REFERENCE TO RELATED APPLICATIONS

This application is a divisional application of U.S. application Ser. No. 13/819,142 filed Feb. 26, 2013, now abandoned, which is a national stage application of PCT/JP2011/069178, filed Aug. 25, 2011, filed under 35 USC § 371, which claims benefit of U.S. Provisional Patent Application No. 61/471,338, filed Apr. 4, 2011, and Japanese Patent Application No. 2010-191039, filed Aug. 27, 2010. The entire contents of each of the above-mentioned priority applications are hereby incorporated by reference in their entirety.

TECHNICAL FIELD

The present invention relates to a substance P (hereinafter, referred to as "SP")—derived peptide, a hemokinin 1 (hereinafter, referred to as "HK-1")—derived peptide, and a therapeutic agent for pain, a therapeutic agent for inflammation, and a therapeutic agent for pruritus containing these peptides. The present invention further relates to a method for screening a therapeutic agent for pain, a therapeutic agent for inflammation, and a therapeutic agent for pruritus using an HK-1 receptor.

BACKGROUND ART

SP is a peptide consisting of 11 amino acids, and the amino acid sequence thereof is:

(SEQ ID NO: 1)
Arg-Pro-Lys-Pro-Gln-Gln-Phe-Phe-Gly-Leu-Met-NH$_2$

[wherein a carboxyl group of a C-terminal methionine is amidated, and the same applies below].

Meanwhile, HK-1 is a peptide consisting of 11 amino acids and the amino acid sequence thereof is:

(SEQ ID NO: 2)
Arg-Ser-Arg-Thr-Arg-Gln-Phe-Tyr-Gly-Leu-Met-NH$_2$.

Both SP and HK-1 belong to the tachykinin peptide family. Here, the term "tachykinin peptide family" refers to a peptide family having FXGLM-NH$_2$ (where X denotes a hydrophobic amino acid) at the C-terminus.

SP is found not only in vertebrates, but also in invertebrates. It is involved in inflammation, pain, itching, muscular contraction, and the like, and it has various functions in an organism. Therefore, the discovery of a novel antagonist against SP is thought to contribute to the development of remedies for suppressing various symptoms in which SP is involved (e.g., pain, inflammation, and itching).

Previous studies have reported that SP is divided into two regions, an N-terminal fragment (SP(1-7): Arg-Pro-Lys-Pro-Gln-Gln-Phe-NH$_2$ (SEQ ID NO: 3)) and a C-terminal fragment (SP(7-11): Phe-Phe-Gly-Leu-Met-NH$_2$ (SEQ ID NO: 4)), wherein these fragments have different functions (Non-patent Document 1). Specifically, SP administered to a rat or a mouse induces pain-related behavior (e.g., scratching behavior). However, pain-related behavior can be suppressed by administration of the N-terminal fragment of SP. On the other hand, pain-related behavior is induced by administration of the C-terminal fragment of SP.

It has also been reported that the N-terminal fragment (SP(1-7): Arg-Pro-Lys-Pro-Gln-Gln-Phe-NH$_2$ (SEQ ID NO: 3)) of SP and the N-terminal fragment (SP(1-8): Arg-Pro-Lys-Pro-Gln-Gln-Phe-Phe-NH$_2$ (SEQ ID NO: 5)) of SP suppress pain-related behavior resulting from SP (Non-patent Documents 2 and 3).

HK-1 is a peptide suggested to be present based on human and rodent TAC4 genes. However, it remains unknown if an HK-1-specific receptor differs from a receptor (neurokinin-1 receptor (NK1R)) for SP belonging to the same family of HK-1.

There is a view suggesting that an HK-1 specific receptor is NK1R based on the facts that: HK-1 has high affinity for NK1R in a manner similar to that of SP (Non-patent Documents 4, 5, and 6); intrathecal administration of HK-1 and SP to rats induces scratching behavior in a manner depending on the concentrations of peptides administered (Non-patent Document 7); and the behavior is also suppressed by known NK1R antagonists (L-703,606) (Non-patent Documents 7 and 8).

However, it is known that (1) intrathecal administration of SP induces thermal hyperalgesia (Non-patent Documents 9 and 10), but HK-1 administration results in no such reaction at all (Non-patent Documents 7 and 11), (2) pre-administration of endokinin C/D (EK C/D) composed of a consensus amino acid sequence corresponding to 12 amino acids from the C-terminal region of endokinin C and endokinin D, which are endokinin peptides belonging to the tachykinin peptide family, can suppress SP-induced scratching behavior, but cannot suppress HK-1-induced scratching behavior (Non-patent Document 8), and (3) evaluation (performed using as an indicator the inhibition of receptor desensitization resulting from treatment of the intracellular signal transduction pathway involved in receptor desensitization using various protein kinase inhibitors) suggests the involvement of different protein kinases in receptor desensitization induced by SP and HK-1 (Non-patent Document 12). Based on these results, it is assumed that receptors (HK-1-preferred receptors) specific to HK-1, which differ from NK1R, are present and the receptor functions thereof are analogous to each other, but are not the same (Non-patent Documents 7, 8, and 13).

PRIOR ART DOCUMENTS

Non-Patent Document

Non-patent Document 1: Michal E. Hall, John M. Stewart, Peptides 4 pp. 763-768 (1983)

Non-patent Document 2: Sakurada T et al., Neurosci Lett. 95 pp. 281-285 (1988)

Non-patent Document 3: Sakurada C et al., J Pharm Sci, 88 pp. 1127-1132 (1999)

Non-patent Document 4: R. A. Duffy, J. A. Hedrick, G. Randolp, C. A. Morgan, M. E. Cohen-Williams, G. Vassileva, J. E. Lachowicz, M. Laverty, M. Maguire, L. -S. Shan, E. Custafson, G. B. Varty, Centrally administered hemokinin-1 (HK-1), a neurokinin NK1 receptor agonist, produces substance P-like behavioral effects in mice and gerbils. Neuropharmacology 45 (2003) 242-250

Non-patent Document 5: O. Morteau, B. Lu, C. Gerard, N. P. Gerard, Hemokinin 1 is a full agonist at the substance P receptor, Nat. Immunol. 2 (2001) 1008

Non-patent Document 6: V. Camarda, A. Rizzi, G. Calo, R. Guerrini, S. Salivadori, D. Regoli, Pharmacological pro-file of hemokinin 1: a novel member of the tachykinin family, Life Sci. 71 (2002) 363-370

Non-patent Document 7: D. Endo, T. Ikeda, Y. Ishida, D. Yoshioka, T. Nishimori, Effect of intrathecal administration of hemokinin-1 on the withdrawal response to noxious thermal stimulation of the rat hind paw, Neurosci. Lett. 392 (2006) 114-117

Non-patent Document 8: R. Naono, T. Nakayama, T. Ikeda, O. Matsushima, T. Nishimori, Leucine at the carboxyl-terminal of endokinin C and D contributes to elicitation of the antagonistic effect on substance P in rat pain processing, Brain Res. 1165 (2007) 71-80

Non-patent Document 9: A. B. Malmberg, T. L. Yaksh, Hyperalgesia mediated by spinal glutamate or substance P receptor blocked by spinal cyclooxygenase inhibition, Science 257 (1992) 1276-1279

Non-patent Document 10: T. Nakayama, R. Naono, T. Ikeda, T. Nishimori, NMDA and AMPA receptors contributes to the maintenance of substance P-induced thermal hyperalgesia, Neurosci. Res. 67(2010) 18-24

Non-patent Document 11: N. Sunakawa, R. Naono, T. Ikeda, O. Matsushima, S. Sakoda, T. Nishimori, The amino-terminal region of hemokinins-1 regulates the induction of thermal hyperalgesia in rats, Neuropeptides 44 (2010) 273-278

Non-patent Document 12: R. Naono, T, Nakayama, T. Ikeda, O. Matsushima, T. Nishimori, Pharmacological characterization of desensitization in scratching behavior induced by intrathecal administration of hemokinin-1 in the rat, Neuropeptides 42 (2008) 47-55

Non-patent Document 13: R. Naono, D. Yoshioka, T. Ikeda, T. Nakayama, T. Nishimori, The common carboxyl-terminal region of novel tachykinin peptide contributes to induce desensitization in scratching behavior of rats, Brain Res. Bull. 71 (2007) 461-465

SUMMARY OF THE INVENTION

Problems to Be Solved by the Invention

As described above, the N-terminal fragments (SP(1-7) and SP(1-8)) of SP are known to suppress pain-related behavior resulting from SP. However, further improvement of the N-terminal fragments of SP is required in view of formulation. Moreover, further peptides having antagonist activity, pain control activity, anti-inflammation activity, and anti-pruritic activity are required.

Furthermore, discovery of an unknown receptor specific to HK-1 is required.

An object of the present invention is to provide peptides having antagonist activity against SP, pain control activity, anti-inflammation activity, and anti-pruritic activity.

Another object of the present invention is to provide a method for searching a therapeutic agent for pain, a therapeutic agent for inflammation, and a therapeutic agent for pruritus using an HK-1 specific receptor.

MEANS FOR SOLVING THE PROBLEM

As a result of intensive studies to achieve the above objects, the present inventors have discovered that the N-terminal fragment (SP(1-5): Arg-Pro-Lys-Pro-Gln-NH$_2$ (SEQ ID NO: 6)) of SP and the N-terminal fragment (HK-1(1-5): Arg-Ser-Arg-Thr-Arg-NH$_2$ (SEQ ID NO: 7)) of HK-1 belonging to the tachykinin peptide family suppress pain-related behavior (scratching behavior) resulting from SP and inflammatory pain induced by formalin administration. They have further discovered that the above suppression effects are sustained for a long time period through substitution of some L-amino acids in the N-terminal fragment (SP(1-5)) of SP and the N-terminal fragment (HK-1(1-5)) of HK-1 with D-amino acids.

Furthermore, they have identified that the HK-1 specific receptor is the G protein coupled receptor (GPR) 83.

The present invention encompasses the following (1) to (20).

(1) Use of GPR83 for screening a compound useful for treating pain, inflammation, or pruritus.

(2) A method for screening a compound useful for treating pain, inflammation, or pruritus, comprising the steps of:
bringing a compound assumed to be an antagonist against the function of an HK-1 receptor into contact with GPR83;
detecting binding of the compound to and/or antagonist activity of the compound against GPR83; and
screening a compound useful for treating pain, inflammation, or pruritus.

(3) The method according to (2), comprising the steps of:
preparing a cell membrane containing GPR83;
bringing a compound assumed to be an antagonist against the function of the HK-1 receptor into contact with the cell membrane; and
confirming whether the compound binds to GPR83 and thus exhibits antagonist activity.

(4) The use according to (1) or the method according to (2) or (3), wherein GPR83 is:
(i) a polypeptide consisting of the amino acid sequence represented by any one of SEQ ID NOS: 17 to 20;
(ii) a polypeptide containing a partial sequence of the amino acid sequence represented by any one of SEQ ID NOS: 17 to 20, and having HK-1 receptor activity;
(iii) a polypeptide comprising the amino acid sequence represented by any one of SEQ ID NOS: 17 to 20, and having HK-1 receptor activity;
(iv) a polypeptide consisting of an amino acid sequence that has a deletion, a substitution, and/or an addition of 1 to 10 amino acids with respect to the amino acid sequence of any one of the polypeptides (i) to (iii), and having HK-1 receptor activity; or
(v) a polypeptide comprising an amino acid sequence that has at least 90% sequence identity with the amino acid sequence of any one of the polypeptides (i) to (iii), and having HK-1 receptor activity.

(5) A pharmaceutical composition for treating pain, inflammation, or pruritus, containing a GPR83 function inhibitor (selected from the group consisting of an antagonist, an antibody, antisense, and siRNA).

(6) Any one of the following peptides (a) to (c) or a pharmaceutically acceptable salt thereof:
(a) a peptide consisting of the amino acid sequence represented by (SEQ ID NO: 7)
            Arg-Ser-Arg-Thr-Arg-NH$_2$

[wherein the C-terminal Arg-NH$_2$ denotes Arg in which a carboxyl group is amidated];
(b) a peptide consisting of the amino acid sequence represented by (SEQ ID NO: 6)
            Arg-Pro-Lys-Pro-Gln-NH$_2$

[wherein the C-terminal Gln-NH$_2$ denotes Gln in which a carboxyl group is amidated]; and
(c) a peptide consisting of an amino acid sequence that has a deletion, a substitution, or an addition of one or several amino acids at a position other than Arg or Lys with respect to the amino acid sequence of the peptide (a) or (b) above, and having at least one activity selected from the group consisting of antagonist activity against substance P, pain control activity, anti-inflammation activity, and anti-pruritic activity
(excluding a peptide consisting of the amino acid sequence represented by Arg-Pro-Lys-Pro-Gln-Gln-Phe-NH$_2$ (SEQ ID NO: 3)

[wherein the C-terminal Phe-NH$_2$ denotes Phe in which a carboxyl group is amidated]; and a peptide consisting of the amino acid sequence represented by Arg-Pro-Lys-Pro-Gln-Gln-Phe-Phe-NH$_2$ (SEQ ID NO: 5)

[wherein the C-terminal Phe-NH$_2$ denotes Phe in which a carboxyl group is amidated]).
(7) Any one of the following peptides (d) to (f) or a pharmaceutically acceptable salt thereof:
(d) a peptide consisting of the amino acid sequence represented by Arg-DTrp-Arg-Thr-Arg-NH$_2$ (SEQ ID NO: 9)

[wherein the DTrp denotes D-tryptophan and the C-terminal Arg-NH$_2$ denotes Arg in which a carboxyl group is amidated];
(e) a peptide consisting of the amino acid sequence represented by Arg-DTrp-Lys-Pro-Gln-NH$_2$ (SEQ ID NO: 8)

[wherein the DTrp denotes D-tryptophan, and the C-terminal Gln-NH$_2$ denotes Gln in which a carboxyl group is amidated]; and
(f) a peptide consisting of an amino acid sequence that has a deletion, a substitution, or an addition of one or several amino acids at a position other than DTrp, Arg, or Lys with respect to the amino acid sequence of the peptide (d) or (e) above, and having at least one activity selected from the group consisting of antagonist activity against substance P, pain control activity, anti-inflammation activity, and anti-pruritic activity.
(8) An antagonist against substance P, consisting of the peptide of (6) or (7) or a pharmaceutically acceptable salt thereof.
(9) A therapeutic agent for pain, containing the peptide of (6) or (7) or a pharmaceutically acceptable salt thereof as an active ingredient.
(10) A therapeutic agent for inflammation, containing the peptide of (6) or (7) or a pharmaceutically acceptable salt thereof as an active ingredient.
(11) A therapeutic agent for pruritus, containing the peptide of (6) or (7) or a pharmaceutically acceptable salt thereof as an active ingredient.

The present invention further encompasses the following embodiments.
(12) A screening agent containing GPR83 for screening a compound useful for treating pain, inflammation, or pruritus.
(13) A GPR83 function inhibitor (selected from the group consisting of an antagonist, an antibody, antisense, and siRNA) for treating pain, inflammation, or pruritus.
(14) Use of a GPR83 function inhibitor (selected from the group consisting of an antagonist, an antibody, antisense, and siRNA) in production of a medicament for treating pain, inflammation, or pruritus.
(15) A method for treating pruritus, pain, or inflammation, comprising administering an effective amount of a GPR83 function inhibitor (selected from the group consisting of an antagonist, an antibody, antisense, and siRNA) to a mammal (e.g., a human) that requires treatment for pain, inflammation, or pruritus.
(16) The peptide according to (6) or (7) or a pharmaceutically acceptable salt thereof for use as a medicament, which is used as a medicament.
(17) The peptide according to (6) or (7) or a pharmaceutically acceptable salt thereof for use in the treatment of pain, inflammation, or pruritus.
(18) A pharmaceutical composition, containing the peptide of (6) or (7) or a pharmaceutically acceptable salt thereof, and a pharmaceutically acceptable carrier.
(19) Use of the peptide according to (6) or (7) or a pharmaceutically acceptable salt thereof in production of a medicament for treating pain, inflammation, or pruritus.
(20) A method for treating pain, inflammation, or pruritus, comprising administration of an effective amount of the peptide of (6) or (7) or a pharmaceutically acceptable salt thereof to a mammal (e.g., a human) that requires treatment for pain, inflammation, or pruritus.

This description includes the contents as disclosed in the descriptions and/or drawings of Japanese Patent Application No. 2010-191039 and U.S. provisional patent application No. 61/471,338, which are priority documents of the present application.

EFFECTS OF THE INVENTION

According to the present invention, a peptide having at least one activity selected from the group consisting of antagonist activity against SP, pain control activity, anti-inflammation activity, and anti-pruritic activity can be provided. Furthermore, through substitution of some L-amino acids with D-amino acids, a peptide having the above activity that can be sustained for a long time period can be provided.

Moreover, through screening a compound using GPR83 that is an HK-1 specific receptor, a compound useful for treating pain, pruritus, pruritus, or the like in which HK-1 is involved can be provided.

EMBODIMENTS FOR CARRYING OUT THE INVENTION

Figure 1:
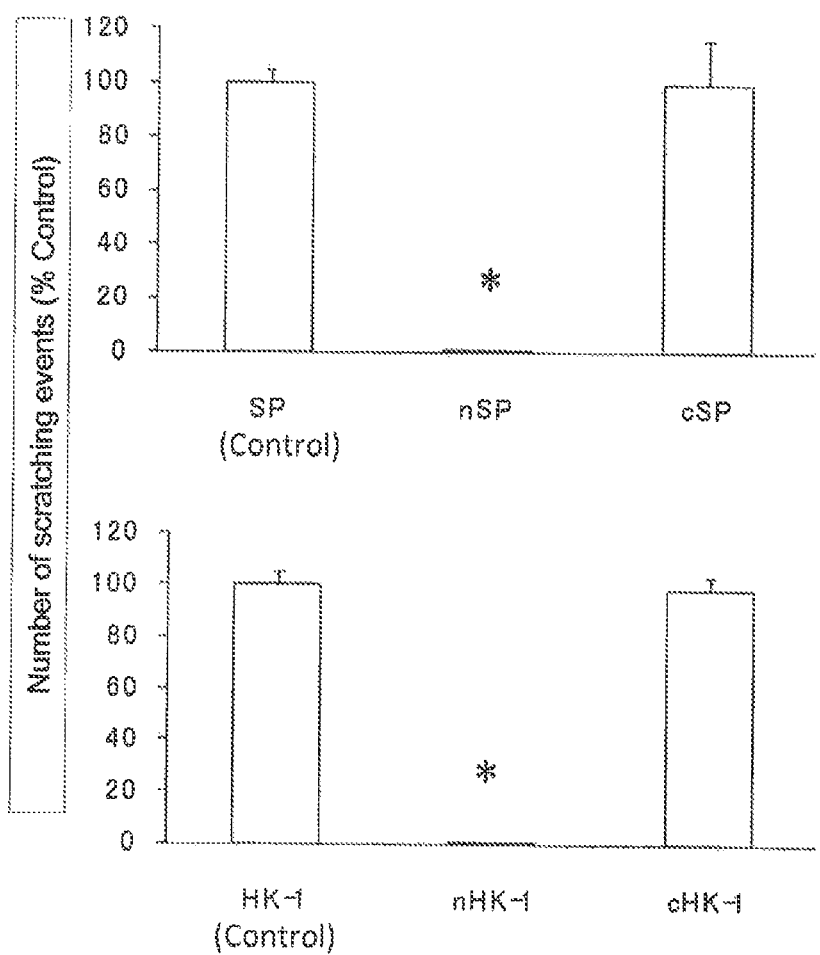
FIG. 1 shows the effects of suppressing SP-induced scratching behavior by SP, nSP (SP(1-5)), cSP (SP(6-11)), HK-1, nHK-1 (HK-1 (1-5)), and cHK-1 (HK-1 (6-11)).

The present invention will be further described in detail.
1. Hemokinin-1-Derived Peptide and Substance P-Derived Peptide The peptide according to the present invention consists of the amino acid sequence represented by

```
                                          (SEQ ID NO: 6)
    Arg-Pro-Lys-Pro-Gln-NH2
or
                                          (SEQ ID NO: 7)
    Arg-Ser-Arg-Thr-Arg-NH2
```

[wherein the C-terminal Gln-NH$_2$ and Arg-NH$_2$ denote Gln and Arg, respectively, in which a carboxyl group is amidated].

Through administration of the peptide according to the present invention to an animal such as a human, pain-related behavior, thermal hyperalgesia, pain, inflammation, itching, and the like resulting from SP can be suppressed. Furthermore, inflammatory pain induced by formalin administration or the like and itching induced by administration of itching inducers can also be suppressed.

Also, the peptide according to the present invention may be peptide each consisting of an amino acid sequence that has a deletion, a substitution, or an addition of 1 or several (e.g., 1 to 3, preferably 1 or 2, and particularly preferably 1) amino acids at a position(s) other than Arg and Lys with respect to the above amino acid sequence(s), and having at least one activity selected from the group consisting of antagonist activity against SP, pain control activity, anti-inflammation activity, and anti-pruritic activity.

Here, the term "antagonist activity against SP" refers to activity of suppressing pain-related behavior, thermal hyperalgesia, pain, inflammation, itching and the like resulting from SP. The terms "pain control activity," "anti-inflammation activity," and "anti-pruritic effect" refer to activity suppressing pain, activity suppressing inflammation, and activity suppressing pruritus. However, examples of pain, inflammation, and pruritus are not limited to those resulting from SP. For example, activity of suppressing inflammatory pain induced by formalin administration is also included herein. Furthermore, activity of suppressing itching induced by administration of an itching inducer represented by histamine or serotonin is also included herein.

In addition, inflammatory pain induced by formalin administration can be regarded as a neuropathic pain model in a broad sense. Furthermore, inflammation induced by administration of carrageenin, which is an inflammatory agent, can also be regarded as a neuropathic pain model in a broad sense. The above activity can be evaluated according to evaluation procedures described in Examples.

The peptide according to the present invention is subjected to substitution of an L-amino acid with D-amino acid, so that the peptide is not easily degraded in vivo and antagonist activity against SP, pain control activity, anti-inflammation activity, and anti-pruritic activity can be sustained for a long time period. Specifically, the present invention also encompasses a peptide consisting of the amino acid sequence represented by

```
                                          (SEQ ID NO: 8)
    Arg-DTrp-Lys-Pro-Gln-NH2
or
                                          (SEQ ID NO: 9)
    Arg-DTrp-Arg-Thr-Arg-NH2
```

[wherein the DTrp denotes D-tryptophan and C-terminal Gln-NH$_2$ and Arg-NH$_2$ denote Gln and Arg, respectively, in which a carboxyl group is amidated].

Also, the peptide according to the present invention may be peptide each consisting of an amino acid sequence that has a deletion, a substitution, or an addition of 1 or several (e.g., 1 or 2, and preferably 1) amino acids at a position(s) other than DTrp, Arg, and Lys with respect to the amino acid sequence of the above peptide, and having at least one activity selected from the group consisting of antagonist activity against SP, pain control activity, anti-inflammation activity, and anti-pruritic activity.

The peptide according to the present invention may be in the form of pharmaceutically acceptable salt. Examples of a pharmaceutically acceptable salt include alkali metal salts (e.g., a sodium salt and a potassium salt), alkaline earth metal salts (e.g., a calcium salt and a magnesium salt), organic acid addition salts (e.g., acetate, maleate, fumarate, tartrate, and citrate), and inorganic acid addition salts (e.g., hydrochloride, sulfate, and phosphate).

The peptide according to the present invention can be chemically synthesized by a known peptide synthesis method. Alternatively, DNA encoding the peptide according to the present invention is introduced into a host, and then the thus expressed peptide according to the present invention is collected, so that the peptide according to the present invention can be obtained.

The peptide according to the present invention has antagonism to the action of SP, and thus the peptide can be used as antagonists against SP.

The involvement of SP in many symptoms (e.g., pain, inflammation, and itching) is known (Pharmacological Reviews 54 (2002) 285-322). Furthermore, formalin induces inflammatory pain, and histamine or serotonin induces itching. Hence, the peptide according to the present invention capable of suppressing symptoms induced by SP, formalin, histamine, and serotonin can be used as an active ingredient for a therapeutic agent for pain, a therapeutic agent for inflammation, and a therapeutic agent for pruritus. Here, examples of "treatment" include, in addition to suppression of the symptoms of a subject who already has the symptoms, suppression of the onset of symptoms in a subject who has no symptom (that is, prevention).

Through the use of a therapeutic agent for pain, a therapeutic agent for inflammation, or a therapeutic agent for pruritus containing the peptide according to the present invention as active ingredients, one or more of the following disease states in humans (physiological disorders, symptoms, or diseases) can be treated: pain related disorders (e.g., hemicrania, neuropathic pain, postoperative pain, chronic pain syndrome); inflammatory diseases (e.g., arthritis and psoriasis); and dermopathy (e.g., atopic dermatitis, contact dermatitis, and herpes zoster).

Examples of the dosage forms of the therapeutic agent for pain, the therapeutic agent for inflammation, or the therapeutic agent for pruritus according to the present invention include, but are not particularly limited to, oral preparations such as tablets, dust formulations, emulsions, capsules, granules, subtle granules, powders, solutions, syrups, suspensions, and elixirs, or parenteral preparations such as injection preparations, drops, suppositories, inhalers, transdermal absorbents, transmucosal absorbents, adhesive preparations, sprays, and ointments.

Examples of pharmaceutical ingredients that can be combined with the peptide according to the present invention include excipients, binders, disintegrators, surfactants, lubricants, fluid accelerators, flavoring agents, colorants, and aroma chemicals.

Examples of excipients include starch, lactose, saccharose, mannite, carboxymethylcellulose, corn starch, and inorganic salts.

Examples of binders include crystalline cellulose, crystalline sodium cellulose-carmellose, methylcellulose, hydroxypropyl cellulose, low substituted hydroxypropyl cellulose, hydroxypropyl methylcellulose, hydroxypropyl methylcellulose phthalate, hydroxypropyl methylcellulose acetate succinate, sodium carmellose, ethyl cellulose, carboxy methyl ethyl cellulose, hydroxyethyl cellulose, wheat starch, rice starch, corn starch, potato starch, dextrin, gelatinized starch, partially gelatinized starch, hydroxypropyl starch, pullulan, polyvinylpyrrolidone, aminoalkyl methacrylate copolymer E, aminoalkyl methacrylate copolymer RS, methacrylate copolymer L, methacrylate copolymer, polyvinyl acetal diethyl aminoacetate, polyvinyl alcohol, gum Arabic, powdered acacia, agar, gelatin, white shellac, tragacanth, purified saccharose, and macrogol.

Examples of disintegrators include crystalline cellulose, methylcellulose, low substituted hydroxypropyl cellulose, carmellose, carmellose calcium, carmellose sodium, croscarmellose sodium, wheat starch, rice starch, corn starch, potato starch, partial gelatinized starch, hydroxypropyl starch, sodium carboxymethyl starch, and tragacanth.

Examples of surfactants include soybean lecithin, sucrose fatty acid ester, polyoxyl stearate, polyoxyethylene hydrogenated castor oil, polyoxyethylene polyoxypropylene glycol, sorbitan sesquioleate, sorbitan trioleate, sorbitan monostearate, sorbitan monopaimitate, sorbitan monolaurate, polysorbate, glyceryl monostearate, sodium lauryl sulfate, and lauromacrogol.

Examples of lubricants include wheat starch, rice starch, corn starch, stearic acid, calcium stearate, magnesium stearate, hydrous silicon dioxide, light anhydrous silicic acid, synthetic aluminum silicate, dried aluminum hydroxide gel, talc, magnesium aluminometasilicate, calcium hydrogen phosphate, anhydrous calcium hydrogen phosphate, sucrose fatty acid ester, waxes, hydrogenated plant oil, and polyethylene glycol.

Examples of fluid accelerators include hydrous silicon dioxide, light anhydrous silicic acid, dried aluminum hydroxide gel, synthetic aluminum silicate, and magnesium silicate.

When the dosage form of the therapeutic agent for pain, the therapeutic agent for inflammation, or the therapeutic agent for pruritus according to the present invention is a solution, a syrup, a suspension, an emulsion, or an elixir, it may contain a taste and flavor corrigent, a colorant, and the like.

Moreover, the therapeutic agent for pain, the therapeutic agent for inflammation, or the therapeutic agent for pruritus according to the present invention may further contain other ingredients. Examples of ingredients that can be contained in the therapeutic agent for pain, the therapeutic agent for inflammation, or the therapeutic agent for pruritus according to the present invention include propionic acid derivative-based nonsteroidal antiinflammatory drugs such as propionic acid derivatives (e.g., ibuprofen, ketoprofen, flurbiprofen, flurbirofen axetil, oxaprozin, fenoprofen, tiaprofenic acid, naproxen, pranoprofen, loxoprofen, aminoprofen, zartoprofen, or salts thereof), non-pyrine-based antipyretic analgesics such as acetaminophen, dimetotiazine mesilate, or salts thereof, antiplasmin agents such as tranexamic acid, epsilon aminocaproic acid, or salts thereof, and anti-inflammatory enzyme drugs such as lysozyme chloride, semialkaline proteinase, serrapeptase, bromelain, or salts thereof.

The contents of the peptide according to the present invention in the therapeutic agent for pain, the therapeutic agent for inflammation, or the therapeutic agent for pruritus according to the present invention can be appropriately varied depending on purposes of administration, routes of administration, dosage forms, and the like. For example, the content ranges from 0.001 mg to 1 mg and preferably ranges from 0.001 mg to 0.01 mg.

The frequency of administration, dosage, and duration of administration for the therapeutic agent for pain, the therapeutic agent for inflammation, or the therapeutic agent for pruritus according to the present invention are not particularly limited and can be appropriately determined depending on disease type, patient age, gender, body weight, or the degree of severity of symptoms, route of administration, and the like. The frequency of administration ranges from once to three times a day and is preferably once a day in the case of external use, for example. The dosage of the peptide according to the present invention contained in the therapeutic agent for pain, the therapeutic agent for inflammation, or the therapeutic agent for pruritus according to the present invention is as described below. Based on the dosage of indomethacin, which is 50 mg for external use and is 1 mg for intravenous injection, it is estimated that the dosage of the peptide for intravenous injection ranges from 0.01 mg to 1 mg per kg of body weight per day and preferably ranges from 0.01 mg to 0.1 mg per kg of body weight, and that the dosage of the peptide for external use is 50 times greater than the dosage for intravenous injection. Also, the duration of administration ranges from 1 to 7 days and preferably ranges from 1 to 2 days, for example.

The routes of administration of the therapeutic agent for pain, the therapeutic agent for inflammation, or the therapeutic agent for pruritus according to the present invention can be appropriately determined by depending on dosage forms or purposes for use. Examples of the routes of administration include peroral administration, parenteral administration (e.g., intrathecal administration, intraperitoneal administration, intravenous administration, intramuscular administration, subcutaneous administration, intrarectal administration, intranasal administration, and sublingual administration) and local administration (e.g., transdermal patches, lotions, solutions, aerosol agents, gel, cream pharmaceuticals, ointments, adhesive skin patches).

2. Screening Method Using HK-1 Specific Receptor

HK-1 is a substance involved in pain, inflammation, and pruritus. Therefore, searching for an antagonist against HK-1 using a receptor specifically binding to HK-1 makes it possible to find a candidate substance useful for treating pain, inflammation, or pruritus.

The present inventors identified G protein coupled receptor (GPR)83 as an HK-1 specific receptor, as described in the following Examples. Hence, a method for screening a compound useful for treating pain, inflammation, or pruritus using GPR83 is provided.

GPR83 has also been identified in mice and the like including humans, and the amino acid sequence thereof is known based on a database such as GenBank. The already clarified amino acid sequences of GPR83 are shown in SEQ ID NOS: 17 to 20. In addition, the term "GPR83" in the present invention refers to a gene or mRNA encoding a GPR83 protein and is used for any of a protein, a gene, and mRNA. Also examples of "GPR83" include a protein, a gene, and mRNA resulting from mutation of some amino acids or bases of the protein, gene, and mRNA, and the fragments thereof.

GPR83 that is used in the screening method according to the present invention may be a full-length GPR83 protein, a peptide fragment thereof having HK-1 receptor activity, or a substance containing the full-length protein as a fragment and having HK-1 receptor activity. Furthermore, a polypeptide comprising an amino acid sequence that has a deletion, a substitution, and/or an insertion of 1 to 10 amino acids, or an amino acid sequence that has at least 90% sequence identity with the amino acid sequence of any one of these polypeptides and having HK-1 receptor activity can also be used herein.

Examples of GPR83 in the present invention include:
(i) a polypeptide consisting of the amino acid sequence represented by any one of SEQ ID NOS: 17 to 20;
(ii) a polypeptide containing a partial sequence of the amino acid sequence represented by any one of SEQ ID NOS: 17 to 20 (preferably, consisting of a partial sequence of the amino acid sequence represented by any one of SEQ ID NOS: 17 to 20), and having HK-1 receptor activity;
(iii) a polypeptide comprising the amino acid sequence represented by any one of SEQ ID NOS: 17 to 20, and having HK-1 receptor activity; or
(iv) a polypeptide consisting of an amino acid sequence that has a deletion, a substitution, and/or an addition of 1 to 10, preferably 1 to 7, and more preferably 1 to 4 amino acids with respect to the amino acid sequence of any one of the polypeptides (i) to (iii), and having HK-1 receptor activity; or
(v) a polypeptide comprising an amino acid sequence that has at least 90%, preferably at least 95%, and more preferably at least 98% sequence identity with the amino acid sequence of any one of the polypeptides (i) to (iii) (preferably consisting of an amino acid sequence that has at least 90%, preferably at least 95%, and more preferably at least 98% sequence identity with the amino acid sequence of any one of the polypeptides (i) to (iii)), and having HK-1 receptor activity.

The screening method using GPR83 that is the HK-1 specific receptor comprises the following steps.
The screening method comprises the steps of:
bringing a compound assumed to be an antagonist against the function of an HK-1 receptor into contact with GPR83; detecting the binding of the compound to and/or antagonist activity of the compound against GPR83; and screening a compound useful for treating pain, inflammation, or pruritus.

More specifically, the screening method comprises the following steps of:
preparing a cell membrane containing GPR83;
bringing a compound assumed to be an antagonist against the function of the HK-1 receptor into contact with the cell membrane; and
confirming whether the compound binds to GPR83, and thus exhibits antagonist activity.

GPR83 can be brought into contact with a compound assumed to be an antagonist against the function of the HK-1 receptor (test compound) by all known means including mixing GPR83 with the compound in the same reaction solution or in the same culture solution, or maintaining them within the same cells, for example. Optimum reaction conditions can be appropriately selected by depending on these means. For example, these means can be performed at room temperature or temperatures appropriate for culture for several minutes to several hours.

A method for detecting the binding of a test compound to and/or antagonist activity of the same against GPR83 after reaction can also be performed by a known means.

EXAMPLES

The present invention will be more specifically described below by referring to Examples, but the technical scope of the present invention is not limited to these Examples.

Example 1

Pharmacological Evaluation 1 for Peptides Consisting of N-Terminal Regions of HK-1 and SP
1. Purpose of Experiment Previous studies reported that N-terminal regions and the C-terminal regions of SP have different functions (Non-patent Document 1). Hence, whether or not the regions had similar effects in our experimental system was examined. In addition, N-terminal regions (nHK1 (HK-1(1-5)) and nSP (SP(1-5))) and C-terminal regions (cHK-1 (HK-1(6-11)) and cSP (SP(6-11))) have the following amino acid sequences.

```
nHK-1:
                                   (SEQ ID NO: 7)
     Arg-Ser-Arg-Thr-Arg-NH2 nSP:
                                   (SEQ ID NO: 6)
     Arg-Pro-Lys-Pro-Gln-NH2 cHK:
                                  (SEQ ID NO: 10)
     Gln-Phe-Tyr-Gly-Leu-Met-NH2 cSP:
                                  (SEQ ID NO: 11)
     Gln-Phe-Phe-Gly-Leu-Met-NH2.
```

2. Experimental Method and Results $10^{-3}$ M (10 nmol/10 µl) HK-1 and SP, the N-terminal regions (nHK-1 and nSP), and the C-terminal regions (cHK-1 and cSP) were administered to intrathecally catheterized rats via catheters. Ethological changes beginning immediately after administration were evaluated using the number of scratching events during a 5-minute period after each peptide administration as an indicator. Here, the expression "$10^{-3}$ M (10 nmol/10 µl) . . . administered" refers to administration of 10 µl (full dose) of a solution containing 10 nmol of a peptide (e.g., nHK-1) (that is, a $10^{-3}$ M solution). The same applies to the following similar expressions. FIG. 1 shows the results. In these graphs, the number of scratching events induced by administration of $10^{-3}$ M (10 nmol/10 µl) SP or HK-1 alone is designated as a control, and is specifically designated as 100%.

As shown in the results, the administration of the N-terminal region (nHK-1 or nSP) alone resulted in no scratching behavior, but the administration of the C-terminal region (cSP or cHK-1) alone resulted in scratching behavior. Hence, it was confirmed that the administration of the C-terminal region, cSP or cHK-1 alone resulted in effects similar to those exhibited with the administration of SP or HK-1 alone.

Example 2

Pharmacological Evaluation 2 for Peptides Consisting of N-Terminal Regions of HK-1 and SP
1. Purpose of Experiment Previous studies reported that the N-terminal regions of SP are peptides having antagonistic effects against SP (Non-patent Documents 2 and 3). Hence, whether or not such regions had similar effects in our experimental system was examined. In addition, the N-terminal regions of SP were evaluated using the peptide SP(1-5) having an amino acid sequence shorter than those of the peptides (SP(1-7) and SP(1-8)) used in Non-patent Documents 2 and 3. Furthermore, HK-1 was similarly evaluated using HK-1 (1-5) as the N-terminal region peptide. Peptides (nSP and nHK-1) used herein had shorter amino acid sequences than those of SP fragment peptides (SP(1-7) and SP(1-8)) reported to date, because such shorter amino acid sequences were assumed to be more advantageous in view of formulation.

2. Experimental Method and Results
(i) Administration Interval

Figure 2:
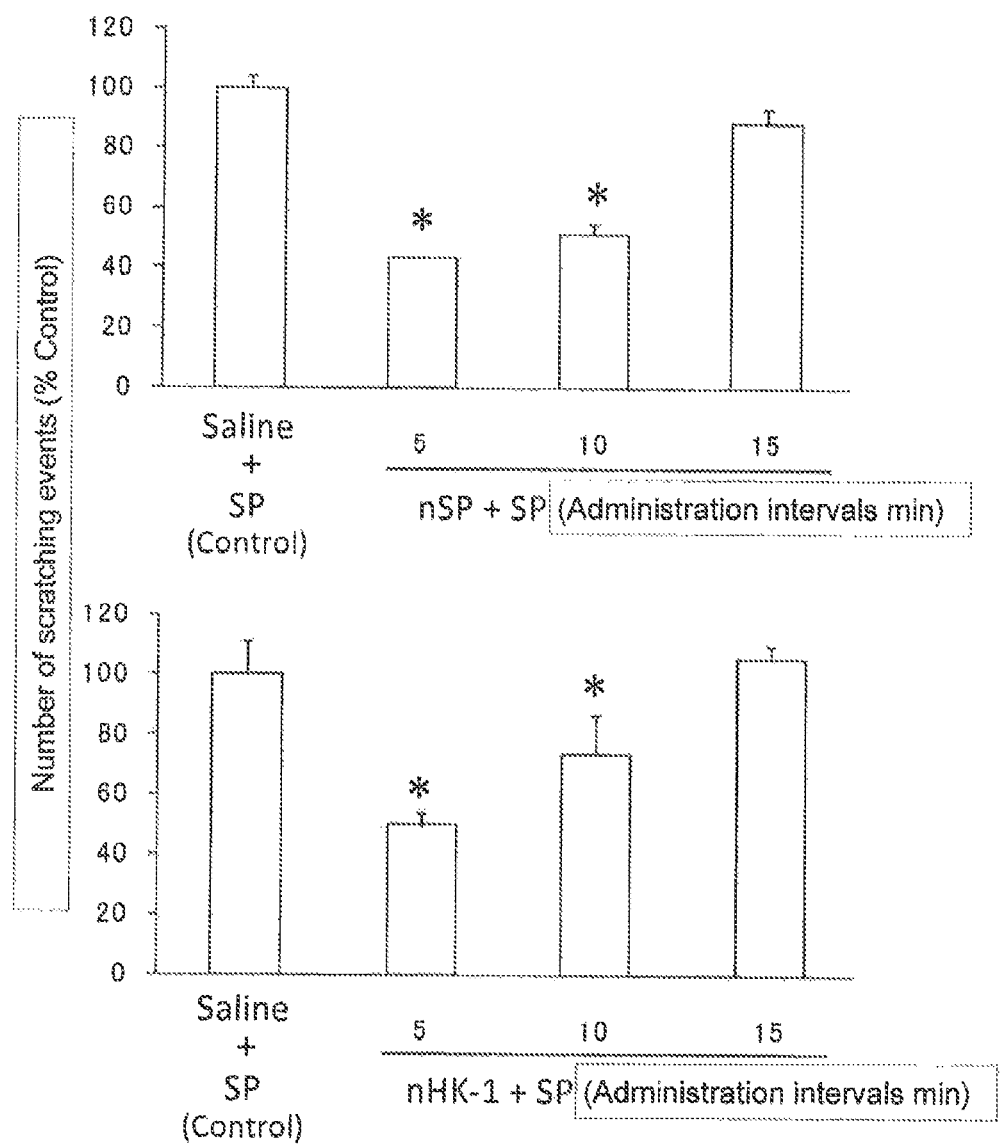
FIG. 2 shows the relationship between the interval of administration of nSP and SP or administration of nHK-1 and SP, and the number of SP-induced scratching events.

FIG. 2 shows the results of administering $10^{-3}$ M (10 nmol/10 µl) N-terminal regions (nSP and nHK-1) to intrathecally catheterized rats via catheters, and varying the interval between administration of nSP and SP and the same between administration of nHK-1 and SP with respect to changes in the number of scratching events induced by administration of $10^{-3}$ M (10 nmol/10 µl) SP. In addition, the number of scratching events induced by SP administration at 5 minutes after saline administration was designated as a control, and was specifically designated as 100%.

Both nSP and nHK-1 were confirmed to significantly suppress the number of scratching events when the interval between administration of SP and nSP or administration of SP and nHK-1 was 5 minutes. The suppression effect was exhibited to a significant degree even at 10 minutes after administration. However, the suppression effect disappeared with an administration interval of 15 minutes.

Figure 3:
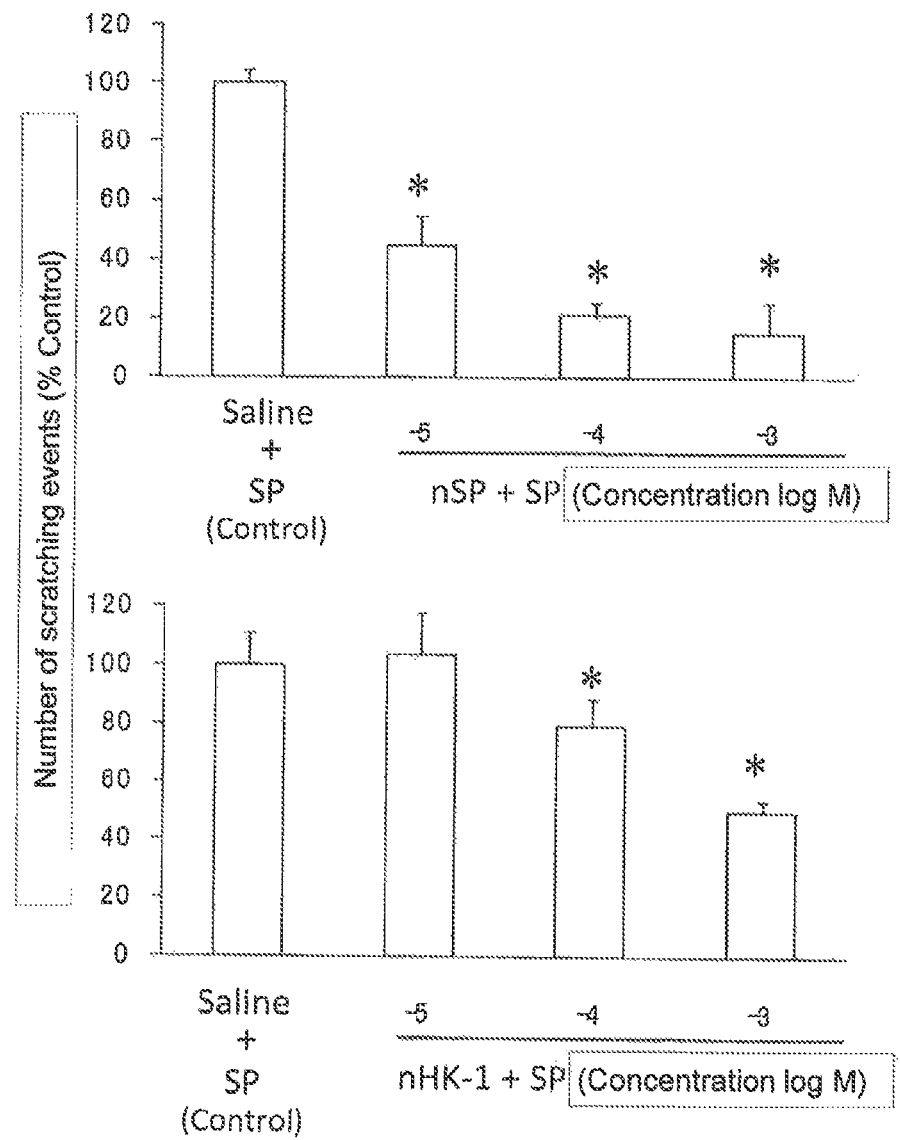
FIG. 3 shows the relationship between the concentrations of nSP and nHK-1 administered and the number of SP-induced scratching events.

Therefore, it was suggested that nSP and nHK-1 are peptides having the effect of suppressing SP-induced scratching behavior.
(ii) Concentration for Administration FIG. 3 shows the results of administering $10^{-5}$ M (100 pmol/10 µl), $10^{-4}$ M (1 nmol/10 µl), and $10^{-3}$ M (10 nmol/10 µl) N-terminal regions (nSP and nHK-1) to intrathecally catheterized rats via catheters, and varying the concentrations of nSP and nHK-1 to be administered with respect to changes in the number of scratching events induced by administration of $10^{-3}$ M (10 nmol/10 µl) SP. In addition, the number of scratching events induced by SP administration at 5 minutes after saline administration was designated as a control and was specifically designated as 100%.

As shown in the results of FIG. 2, both nSP and nHK-1 significantly suppressed the number of scratching events when the interval between administration of nSP and SP or administration of nHK-1 and SP was 5 minutes. This administration interval was employed in the following examples.

Preadministration of $10^{-5}$ M (100 pmol/10 µl), $10^{-4}$ M (1 nmol/10 µl), or $10^{-3}$ M (10 nmol/10 µl) N-terminal region (nSP) suppressed scratching behavior resulting from SP administration. Specifically, in the case of $10^{-3}$ M, an effect of suppressing the number of scratching events was exhibited significantly. Meanwhile, when $10^{-5}$ M (100 pmol/10 µl), $10^{-4}$ M (1 nmol/10 µl), or $10^{-3}$ M (10 nmol/10 µl) N-terminal region (nHK-1) was pre-administered, preadministration of $10^{-3}$ M nHK-1 resulted in an effect of significantly suppressing scratching behavior resulting from SP administration.

Therefore, it was suggested that $10^{-3}$ M nSP and $10^{-3}$ M nHK-1 have effects of significantly suppressing SP-induced scratching behavior.

Example 3

Identification of Amino Acids Involved in the Suppression Effects of Peptides (Consisting of the N-Terminal Regions of HK-1 and SP) on SP
1. Purpose of Experiment It was suggested as shown in FIG. 2 and FIG. 3 that nSP and nHK-1 are peptides having effects of suppressing SP-induced scratching behavior. Hence, in order to specify amino acids involved in the pharmacological effects of these peptides, peptides were synthesized by substituting Arg and Lys (from among amino acids of nSP and nHK-1) with Leu. Then, the pharmacological effects of each synthetic peptide were evaluated using as indicators differences in changes in SP-induced scratching behavior resulting from preadministration of these peptides.

2. Experimental Method and Results $10^{-3}$ M (10 nmol/10 µl) N-terminal regions (nSP and nHK-1) and the following peptides subjected to substitution were administered to intrathecally catheterized rats via catheters.

```
Leu¹-nSP:
                             (SEQ ID NO: 12)
Leu-Pro-Lys-Pro-Gln-NH₂

Leu³-nSP:
                             (SEQ ID NO: 13)
Arg-Pro-Leu-Pro-Gln-NH₂

Leu¹-nHK-1:
                             (SEQ ID NO: 14)
Leu-Ser-Arg-Thr-Arg-NH₂

Leu³-nHK-1:
                             (SEQ ID NO: 15)
Arg-Ser-Leu-Thr-Arg-NH₂

Leu⁵-nHK-1:
                             (SEQ ID NO: 16)
Arg-Ser-Arg-Thr-Leu-NH₂
```

Figure 4:
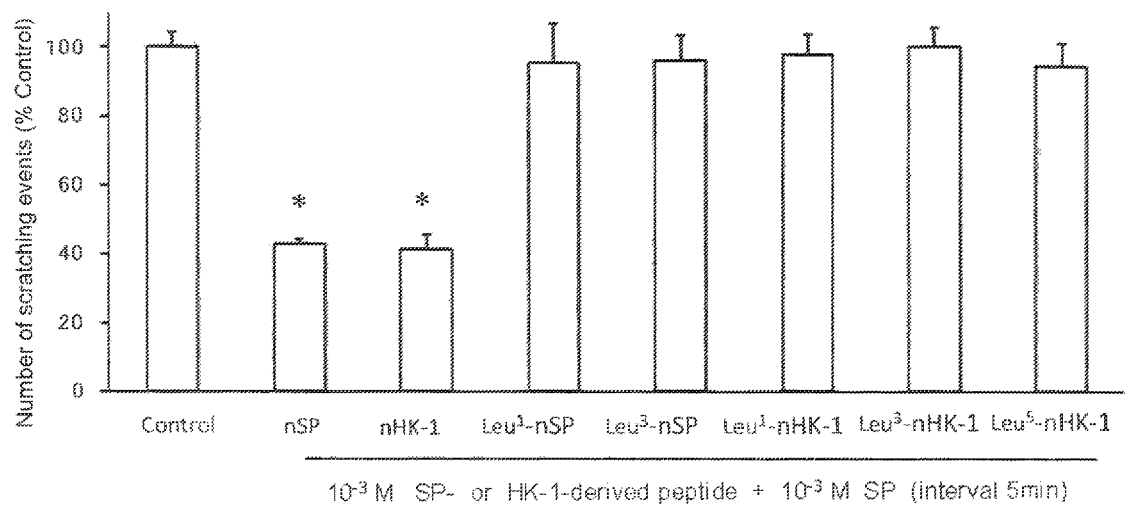
FIG. 4 shows the effects of suppressing SP-induced scratching behavior exhibited by the peptide in which Arg or Lys was substituted with Leu.

5 minutes after administration, the number of scratching events induced by administration of $10^{-3}$ M (10 nmol/10 µl) SP was evaluated. In addition, the number of scratching events induced by administration of $10^{-3}$ M SP at 5 minutes after saline administration was designated as a control and was specifically designated as 100%. FIG. 4 shows the results.

As a result, preadministration of nSP and that of nHK-1 resulted in significant effects of suppressing SP-induced scratching behavior. However, preadministration of all substituted peptides resulted in the disappearance of the effect exhibited by nSP and nHK-1 to suppress SP-induced scratching behavior.

Accordingly, peptides prepared by substitution of Arg and Lys with Leu were confirmed to lose the suppression effect, suggesting that Arg and Lys play important roles in exhibition of the suppression effect by nSP and nHK-1.

Example 4

Identification of Amino Acids Involved in Sustainment of the Suppression Effects of Peptides (Consisting of N-Terminal Regions of HK-1 and SP) on SP
1. Purpose of Experiment FIG. 2 and FIG. 3 suggested that nSP and nHK-1 are peptides having the effect of suppressing SP-induced scratching behavior. Hence, in order to sustain the pharmacological effects of nSP and nHK-1 peptides.

$_D$Trp$^2$-nSP:
(SEQ ID NO: 8)
Arg-DTrp-Lys-Pro-Gln-NH$_2$,
and $_D$Trp$^2$-nHK-1:
(SEQ ID NO: 9)
Arg-DTrp-Arg-Thr-Arg-NH$_2$ were synthesized. The pharmacological effects of each synthetic peptide were evaluated using as an indicator whether or not changes in scratching behavior induced by SP administration occur with preadministration of these synthetic peptides.

Figure 5:
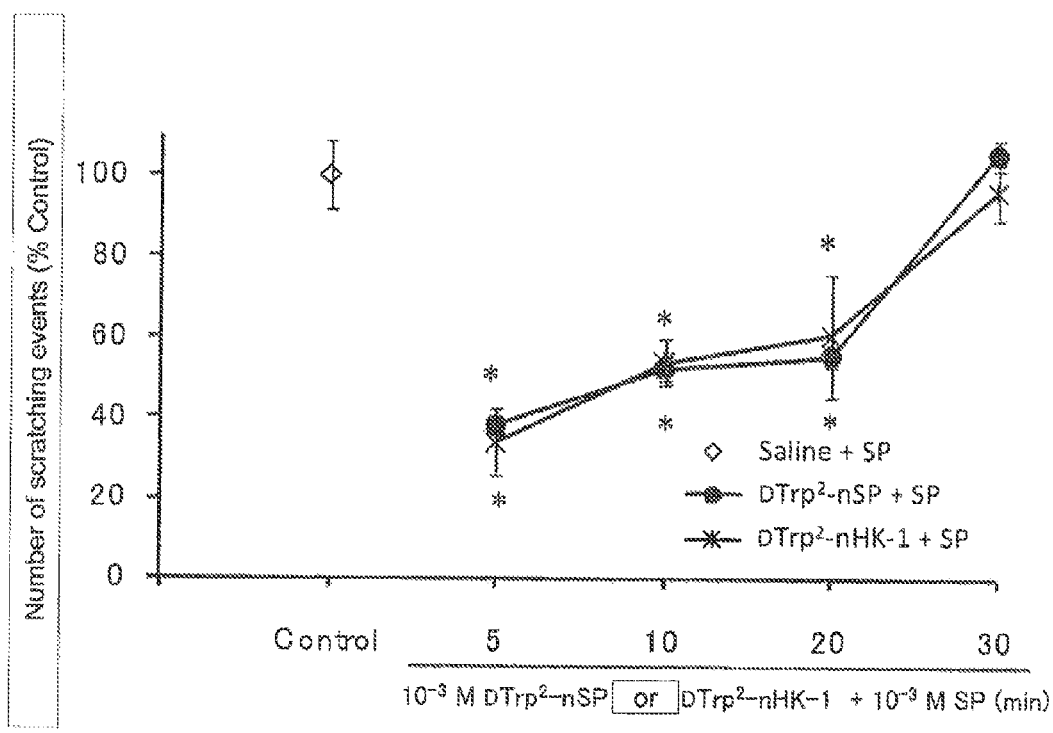
FIG. 5 shows the effects of suppressing SP-induced scratching behavior exhibited by the peptide in which D-tryptophan was introduced.

The reason for using $_D$Trp at position 2 is as follows. Arg and Lys play important roles in exhibition of the suppression effect by nSP and nHK-1 (as revealed by the results in FIG. 4). Accordingly, it was assumed that the suppression effect can be efficiently achieved by synthesizing a peptide via substitution with $_D$Trp at position 2 so as to have Arg and Lys and achieve a long-lasting suppression effect. Hence, such a synthetic peptide was used herein.
2. Experimental Method and Results $10^{-3}$ M (10 nmol/10 μl) $_D$Trp$^2$-nSP and $_D$Trp$^2$-nHK-1 were administered to intrathecally catheterized rats via catheters, and then the number of scratching events induced by administration of $10^{-3}$ M (10 nmol/10 μl) SP was evaluated. FIG. 5 shows the results of varying the interval between administration of $_D$Trp$^2$-nSP and SP and the same between administration of $_D$Trp$^2$-nHK-1 and SP. In addition, the number of scratching events induced by SP administration at 5 minutes after saline administration was designated as a control and was specifically designated as 100%.

Both $_D$Trp$^2$-nSP and $_D$Trp$^2$-nHK-1 were confirmed to significantly suppress the number of scratching events when the interval between administration of SP and $_D$Trp$^2$-nSP or administration of SP and $_D$Trp$^2$-nHK-1 was 5 minutes. A suppression effect was significantly exhibited even at 20 minutes after administration. However, the suppression effect disappeared in the case of an administration interval of 30 minutes.

The suppression effects of nSP and nHK-1 on SP-induced scratching behavior disappeared at 15 minutes after administration, but $_D$Trp$^2$-nSP and $_D$Trp$^2$-nHK-1 maintained significant suppression effects even at 20 minutes after administration. It was suggested that through incorporation of $_D$Trp into the amino acid sequences of nSP and nHK-1, the duration of the effect is prolonged.

Example 5

Pain Control Effect of Peptides Consisting of the N-Terminal Regions of HK-1 and SP
1. Purpose of Experiment In this experiment, the effects of intrathecal preadministration of nSP and nHK-1 on pain behavior following intraplantar administration of formalin were confirmed.
2. Experimental Method and Results $10^{-2}$ M (100 nmol/10 μl) nSP and nHK-1, or saline (10 μl) was administered to intrathecally catheterized rats via catheters, and then 5 minutes later, 50 μl of 2% formalin was administered subcutaneously to the hind paws of rats. The number of flinching events (pain behavior) was determined for a 60-minute period after formalin administration, so that the degree of pain was evaluated. During the 10-minute period after formalin administration (referred to as phase I), pain behavior was determined once every 2 minutes (1 minute per determination). During the period from 10 minutes to 60 minutes after formalin administration (referred to as phase 11), pain behavior was determined once every 5 minutes (1 minute per determination), so that the degree of pain was evaluated. During phase I, behavior (phasic pain) resulting from chemical stimulation accompanying formalin administration was observed. During phase II, tonic pairs following the phasic pain was observed.

Figure 6:
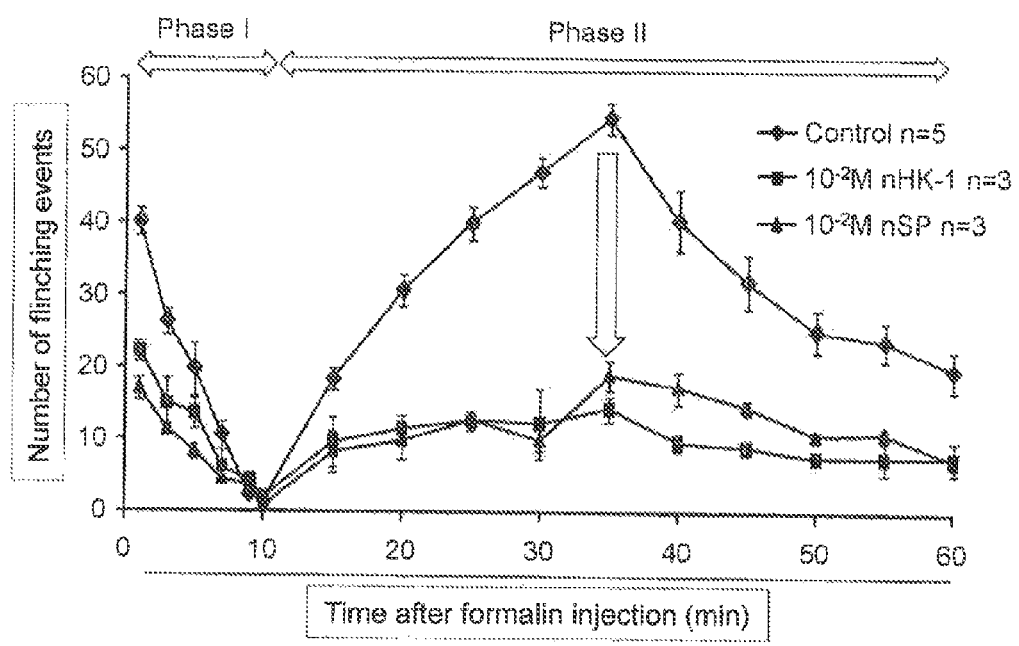
FIG. 6 shows the effects of suppressing formalin-induced inflammatory pain by nSP and nHK-1.
Figure 7:
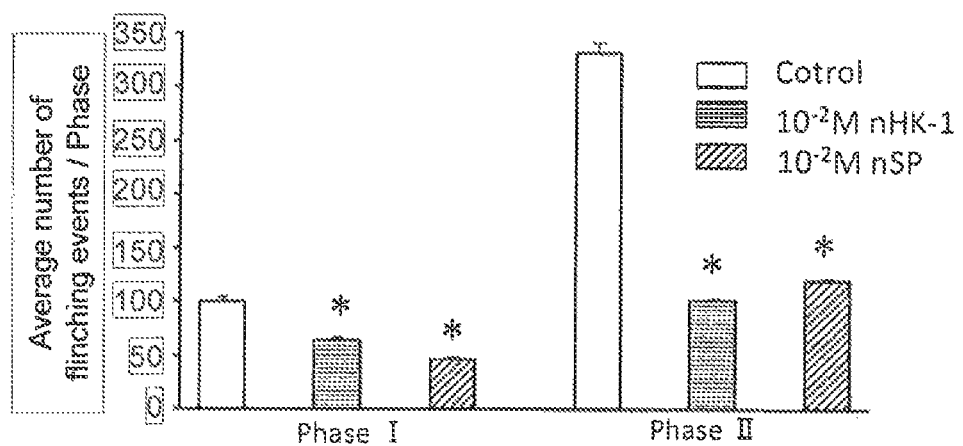
FIG. 7 shows the effects of suppressing formalin-induced inflammatory pain by nSP and nHK-1.

FIG. 6 shows the results. The horizontal axis indicates time (minutes) after formalin administration and the vertical axis indicates the determined number of pain behavior events per minute. FIG. 7 shows the average numbers of pain behavior events determined during phase I and phase II.

It was confirmed for nSP and nHK-1 that pain behavior decreased significantly during both phase I and phase II.

Example 6

Effect of Peptides (Consisting of N-Terminal Regions of HK-1 and SP) to Suppress Itching Following Administration of Itching Inducers
1. Purpose of Experiment As with the results in FIG. 5, the suppression effect of nSP and nHK-1 on SP-induced scratching behavior (scratching behavior induced by intrathecal administration of SP) disappeared at 15 minutes after administration, but $_D$Trp$^2$-nSP and $_D$Trp$^2$-nHK-1 maintained significant suppression effects even at 20 minutes after administration. It was suggested that through incorporation of $_D$Trp into the amino acid sequences of nSP and nHK-1, the effects are maintained for a long time period. Accordingly, the effects of the intrathecal administration of peptides on itching behavior in subcutaneous tissue were confirmed. $10^{-2}$ M (100 nmol/10 μl) $_D$Trp$^2$-nSP (Arg-DTrp-Lys-Pro-Gln-NH$_2$ (SEQ ID NO: 8)) and $_D$Trp$^2$-nHK-1 (Arg-DTrp-Arg-Thr-Arg-NH$_2$ (SEQ ID NO: 9)) were each synthesized and administered to intrathecally catheterized rats via catheters. Histamine and serotonin (5-HT) known as endogenous itching inducers were each administered to the subcutaneous tissue of the nape of the neck. Evaluation was performed using as an indicator whether or not peptide intrathecal pre-administration caused changes in itching behavior following the administration of the itching inducers.
2. Experimental Method and Results Immediately after intrathecal administration of $10^{-2}$ M (100 nmol/10 μl) $_D$Trp$^2$-nSP, $_D$Trp$^2$-nHK-1, or saline (10 μl)

to intrathecally catheterized rats via catheters, an itching inducer ($10^{-3}$ M histamine (0.25 mg/50 µl) or $1.13 \times 10^{-4}$ M 5-HT (0.25 mg/50 µl)) was subcutaneously administered to the nape of the neck, and then itching behavior was determined for 20 minutes, thereby evaluating the degree of itching.

Figure 8:
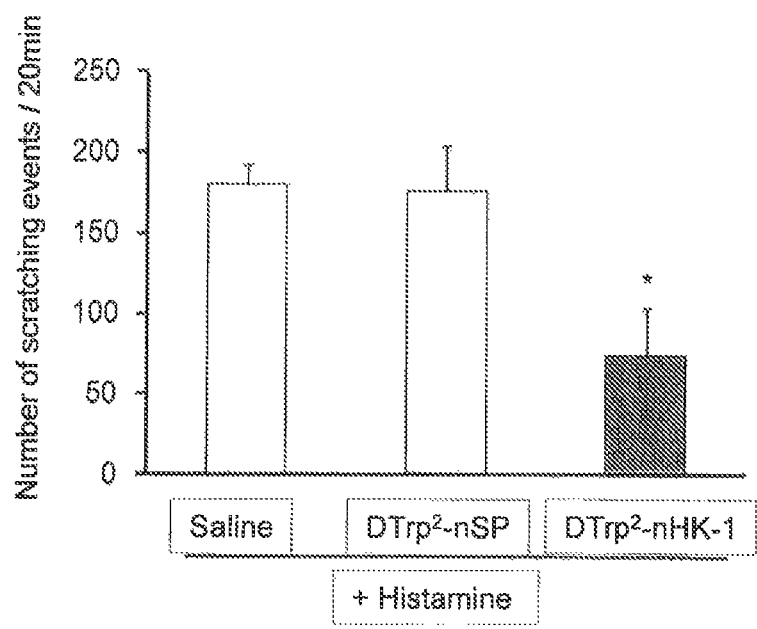
FIG. 8 shows the effects of suppressing histamine-induced pruritus by $_D$Trp$^2$-nSP and $_D$Trp$^2$-nHK-1.
Figure 9:
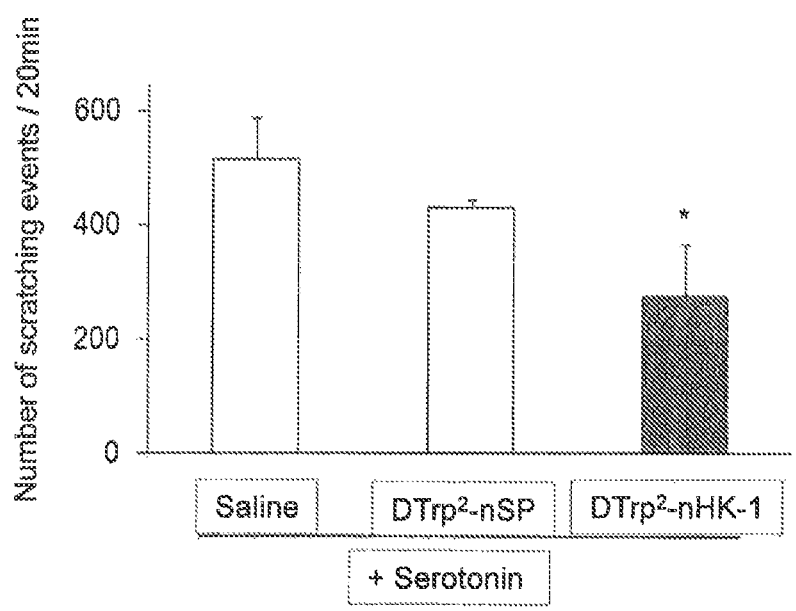
FIG. 9 shows the effects of suppressing serotonin-induced pruritus by $_D$Trp$^2$-nSP and $_D$Trp$^2$-nHK-1.

FIG. 8 and FIG. 9 show itching behavior resulting from administration of histamine and 5-HT. The vertical axis indicates the determined number of scratching events for a 20-minute period after histamine and 5-HT administration. The horizontal axis indicates $_D$Trp$^2$-nSP, $_D$Trp$^2$-nHK-1, and saline administered.

In FIG. 8, $_D$Trp$^2$-nHK-1 administration significantly lowered itching events resulting from histamine administration, but no difference was found in itching behavior between $_D$Trp$^2$-nSP administration and saline administration. Similarly in FIG. 9, $_D$Trp$^2$-nHK-1 administration significantly lowered the degree of itching behavior resulting from 5-HT administration, but no difference was found in the degree of itching behavior between $_D$Trp$^2$-nSP administration and saline administration. These results suggested that histamine-induced itching and 5-HT-induced itching are significantly suppressed by intrathecal pre-administration of $_D$Trp$^2$-nHK-1. In view of the results of Examples 1 to 5, it is assumed that nHK-1 in which $_D$Trp is not introduced suppresses histamine-induced itching and 5-HT-induced itching in a manner similar to that of $_D$Trp$^2$-nHK-1.

Example 7

BLAST Search for HK-1 Specific Receptor Candidate Substances
1. Purpose
It is suggested based on the conventional findings concerning HK-1 that an HK-1 specific receptor differs from NK1R, but has structural similarity therewith to some extent. Hence, BLAST search of GenBank was performed.
2. Experimental Method and Results
BLAST search was performed taking the NK1R amino acid sequence into consideration. Four genes (NK3R, NK2R, GPR83, and GPR15-like) were considered to be HK-1 specific receptor candidate genes. These genes have 60%, 50%, 35%, and 29% homology, respectively, with NK1R.

NKB and NKA are already known to be specific agonists of NK3R and NK2R, respectively. However, GPR83 and GPR15-like are orphan receptors with unknown ligands. Hence, the two latter receptors are thought to be HK-1 specific receptor candidates. Here, GPR83 has other names (GIR, JP05, and GPR 72), and GIR has 31% to 34% homology with NK1R (a tachykinin receptor), so that GIR is thought to belong to the tachykinin receptor family (D. Wang, J. P. Herman, L. M. Pritchard, R. H. Spitzer, R. L. Ahlbrand, G. J. Kramer, F. Petty, F. R. Sallee, N. M. Richtand, Cloning, expression, and regulation of glucocorticoid-induced receptor in rat brain: effect of repetitive amphetamine, J. Neurosci, 15 (2001) 9027-9035). Therefore, an agonist of GIR is likely a tachykinin peptide.

Example 8

NK1R Knockdown Effect
1. Purpose of Experiment
First, the NK1R knockdown effect by NK1R siRNA was confirmed.

2. Experimental Method and Results
(1)

```
NK1R siRNA # 1
sense
                                (SEQ ID NO: 21)
5'-CAACAGGACUUAUGAGAAATT-3' antisense
                                (SEQ ID NO: 22)
5'-UUUCUCAUAAGUCCUGUUGTT-3'

NK1R siRNA # 2
sense
                                (SEQ ID NO: 23)
5'-CAUCAGUGCAGGUGAUUAUTT-3' antisense
                                (SEQ ID NO: 24)
5'-AUAAUCACCUGCACUGAUGTT-3'

NK1R siRNA # 3
sense
                                (SEQ ID NO: 25)
5'-GCAGAGAACUUCACAGGAATT-3' antisense
                                (SEQ ID NO: 26)
5'-UUCCUGUGAAGUUCUCUGCTT-3'

MM siRNA # 1
sense
                                (SEQ ID NO: 27)
5'-AUCCGCGCGAUAGUACGUATT-3' antisense
                                (SEQ ID NO: 28)
5'-UACGUACUAUCGCGCGGAUTT-3'

MM siRNA # 2
sense
                                (SEQ ID NO: 29)
5'UUACGCGUAGCGUAAUACGTT-3' antisense
                                (SEQ ID NO: 30)
5'-CGUAUUACGCUACGCGUAATT-3'

MM siRNA # 3
sense
                                (SEQ ID NO: 31)
5'-UAUUCGCGCGUAUAGCGGUTT-3' antisense
                                (SEQ ID NO: 32)
5'-ACCGCUAUACGCGCGAAUATT-3'
```

(2) Verification of Knockdown Effect
siRNA was prepared using an HVJ Envelop Vector Kit (ISHIHARA SANGYO KAISHA, LTD) according to the protocols of the kit. 10 µl of an siRNA solution was administered to intrathecally catheterized rats via catheters. With administration of only HVJ-E and administration of mismatch siRNA as controls, time-course changes in scratching events resulting from SP or HK-1 were evaluated. As a result, no changes were observed in the number of scratching events induced by SP or in the same induced by HK-1. Therefore, it was considered that administration of only HVJ-E or pretreatment with MM siRNA has almost no effect on scratching behavior induced by SP or HK-1.

Figure 10:
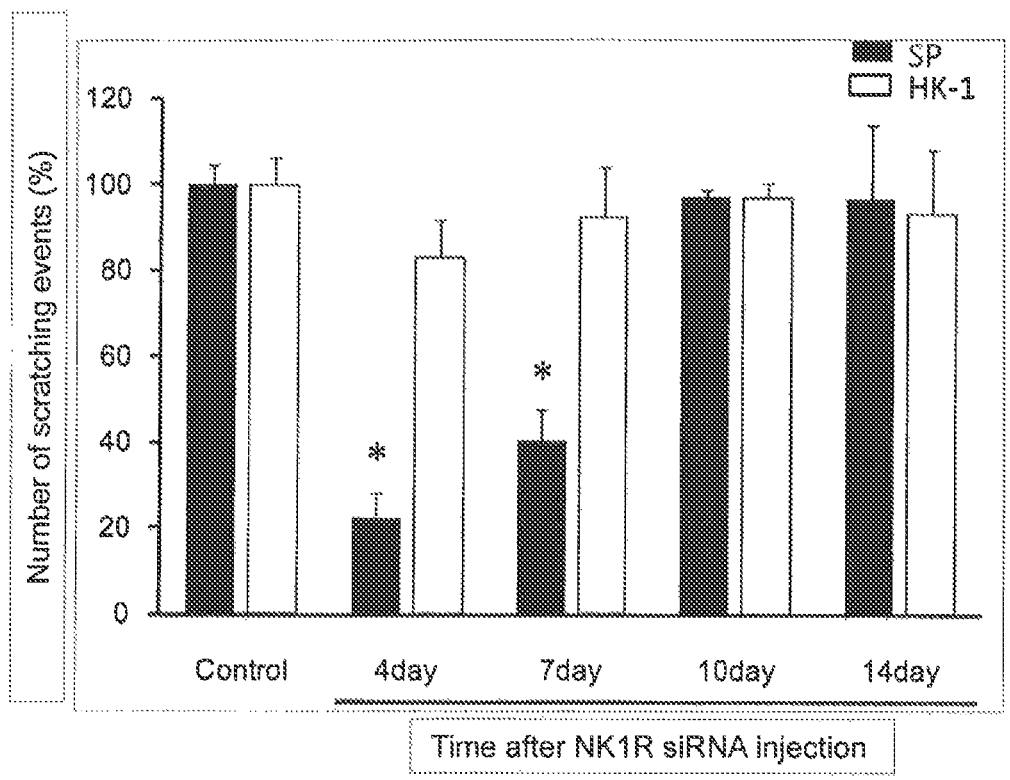
FIG. 10 shows the effects of suppressing SP- and HK-1-induced scratching behavior by NK1R siRNA.

Next, NK1R siRNA was intrathecally administered and then SP was intrathecally administered on days 4, 7, 10, and 14. As a result, suppressed scratching behavior was observed over time in the group to which SP had been administered, such that a significant suppression effect of 49±14.6 was exhibited on day 4 after administration of siRNA (FIG. 10). The number of SP-induced scratching events was gradually recovered after siRNA administration. The number of scratching events decreased to 20% of the control level on day 4 after siRNA administration, but it recovered to 40% of the control level on day 7 after siRNA administration, and recovered to the control level on day 10 and day 14.

Based on these data concerning the number of scratching events as a result of intrathecal administration of SP, it was confirmed that NK1R siRNA administration exhibited the effect of suppressing scratching behavior until at least 7 days after siRNA administration. Therefore, it was suggested by the results that when NK1R expression in the dorsal horn was suppressed by NK1R siRNA, reactivity to SP decreased, and furthermore, the fact that SP is an agonist of NK1R could be re-evaluated.

Next, the number of scratching events resulting from HK-1 administration was evaluated over time after intrathecal administration of NK1R siRNA. The results differed from time-course changes in scratching behavior resulting from SP administration. Specifically, the number of scratching events resulting from intrathecal administration of HK-1 was evaluated on days 4, 7, 10, and 14 after NK1R siRNA administration. As a result, on all dates, the results were the same as those of the control data (FIG. 10). In the group to which SP had been administered, significantly fewer scratching events were observed on days 4 and 7 after NK1R siRNA administration. However, in the group to which HK-1 had been administered, no such effect was exhibited. Therefore, it was inferred that HK-1-induced scratching behavior did not take place via NK1R. Hence, it is unlikely that HK-1 is an agonist of NK1R.

Moreover, EKC/D pre-administration suppressed SP-induced scratching behavior but did not suppress HK-1-induced scratching behavior. It was thus suggested that EKC/D is an NK1R specific antagonist (R. Naono, T. Nakayama, T. Ikeda, O. Matsushima, T. Nishimori, Leucine at the carboxyl-terminal of endokinin C and D contributes to elicitation of the antagonistic effect on substance P in rat pain processing, Brain Res. 1165 (2007) 71-80). Therefore, the result of NK1R knockdown by NK1R siRNA administration is analogous to the result of EKC/D administration. An HK-1 specific receptor is still unknown. However, it is considered that when HK-1 is compared with SP, an agonist of NK1R may be SP rather than HK-1.

Example 9

GPR83 Knockdown Effect
1. Purpose of Experiment
GPR83 knockdown effect by GPR83 siRNA was confirmed.
2. Experimental Method and Results
(1)

```
GPR83 siRNA # 1
sense
                                  (SEQ ID NO: 33)
5'-GCACAUGGGUGUUUGGGAATT-3' antisense
                                  (SEQ ID NO: 34)
3'-UUCCCAAACACCCAUGUGCTT-3'

GPR83 siRNA # 2
sense
                                  (SEQ ID NO: 35)
5'-CCACUGUGGCCGUGAGUUATT-3' antisense
                                  (SEQ ID NO: 36)
3'-UAACUCACGGCCACAGUGGTT-3'

GPR83 siRNA # 3
sense
                                  (SEQ ID NO: 37)
5'-GGGAGGAGCUUCAGCCAUATT-3' antisense
                                  (SEQ ID NO: 38)
3'-UAUGGCUGAAGCUCCUCCCTT-3'
```

(2) Verification of Knockdown Effect
GPR83 siRNA was prepared and then intrathecally administered to rats in a manner similar to that in Example 8.

Figure 11:
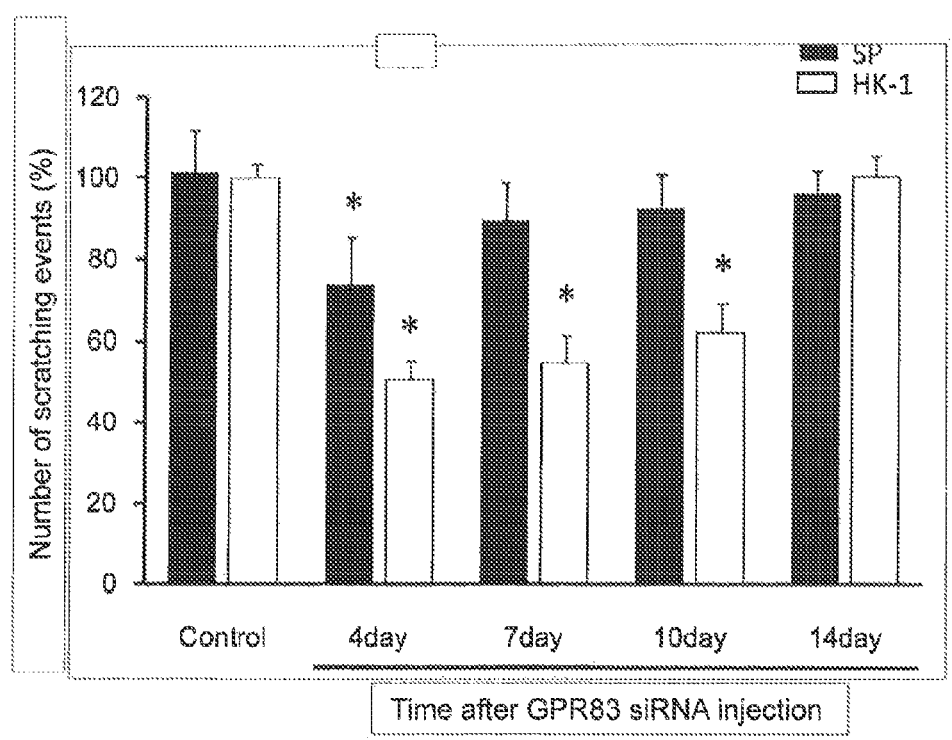
FIG. 11 shows the effects of suppressing SP- and HK-1-induced scratching behavior by GPR83 siRNA.

After GPR83 siRNA administration, the number of scratching events resulting from SP administration over time remained almost unchanged. Furthermore, the number of scratching events induced by SP on days 4, 7, 10, and 14 after GPR83 siRNA administration did not show a significant difference from the control level (FIG. 11). This greatly differed from the results in the case of NK1R siRNA as shown in FIG. 10. The results suggest that GPR83 siRNA has almost no effect on SP-induced scratching behavior. Therefore, it was suggested that GPR83 may not be an SP specific receptor.

Meanwhile, the results of administering GPR83 siRNA to the group to which HK-1 had been administered differed from time-course changes in HK-1-induced scratching behavior with NK1R siRNA administration (FIG. 10). A significant decrease was observed in the number of HK-1-induced scratching events on day 4 after GPR83 siRNA administration, such that the number of scratching events was 210±18.9 (FIG. 11). Moreover, the suppression effect was sustained until day 10 after siRNA administration, and thus a significant decrease was observed in the number of scratching events, compared with the control level. Also, on day 14 after GPR83 siRNA administration, the number of scratching events induced by HK-1 had recovered to the control level. Therefore, it is considered that since GPR 83 is involved in HK-1-induced scratching behavior, HK-1 is an agonist of GPR 83.

Furthermore, interestingly, a knockdown effect by NK1R siRNA (determined using SP-induced scratching behavior as an indicator) was sustained for 7 days, but in the case of knockdown by GPR83 siRNA, HK-1-induced scratching behavior was sustained for 10 days. Accordingly, it is confirmed that the duration of the knockdown effect by NK1R siRNA differs from that of the knockdown effect by GPR83 siRNA. Moreover, each siRNA was administered in a single dose (the same amount and the same concentration). Hence, such a difference in knockdown effect means that the time required for GPR83 to appear on the receptor surface and then return into cells (trafficking) differs from that of NK1R.

Example 10

GPR15-Like Knockdown Effect
1. Purpose of Experiment
The GPR15-like knockdown effect by GPR15-like siRNA was confirmed.
2. Experimental Method and Results
(1)

```
GPR15-like siRNA # 1
sense
                                  (SEQ ID NO: 39)
5'-GAUCAAAGCUGCAAUCAUATT-3' antisense
                                  (SEQ ID NO: 40)
5'-UAUGAUUGCAGCUUUGAUCTT-3'
```

```
                            -continued
GPR15-like siRNA # 2
sense
                                          (SEQ ID NO: 41)
5'-CCAAUGAAACCAAGGCUAATT-3' antisense
                                          (SEQ ID NO: 42)
5'-UUAGCCUUGGUUUCAUUGGTT-3'

GPR15-like siRNA # 3
sense
                                          (SEQ ID NO: 43)
5'-GGACAUUUAUCUUGCUGUATT-3' antisense
                                          (SEQ ID NO: 44)
5'-UACAGCAAGAUAAAUGUCCTT-3'
```

(2) Verification of Knockdown Effect

GPR15-like siRNA was prepared and then intrathecally administered to rats in a manner similar to that in Example 8.

Figure 12:
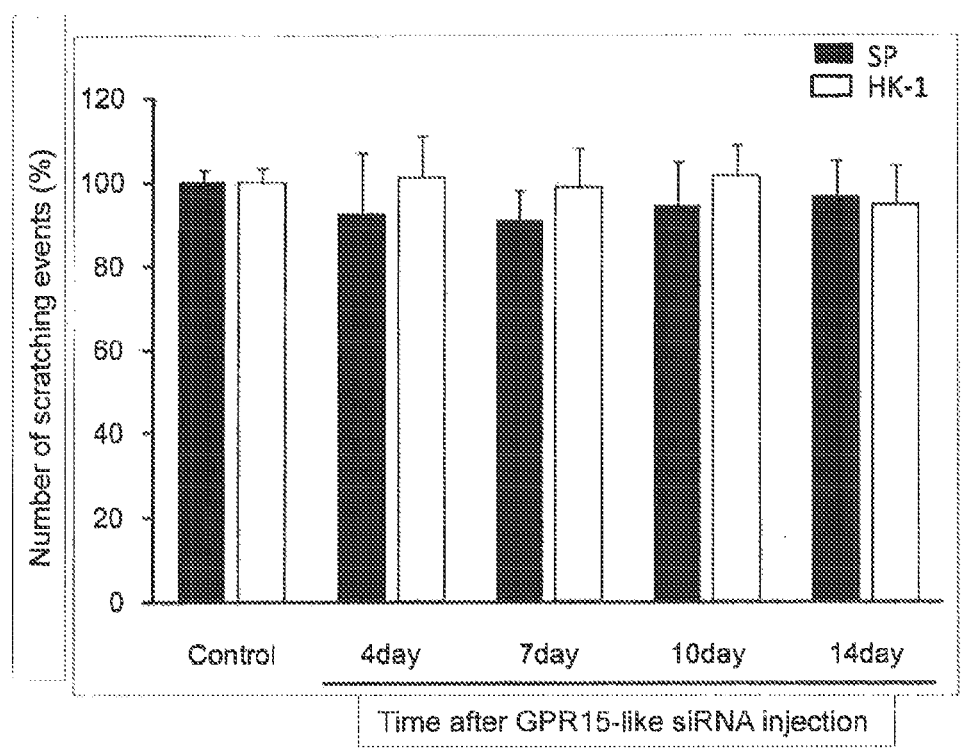
FIG. 12 shows the effects of suppressing SP- and HK-1-induced scratching behavior by GPR15-like siRNA.

SP- or HK-1-induced scratching behavior on days 4, 7, 10, and 14 after GPR15-like siRNA administration did not show a significant difference from the control level. Experimental results on all days were at levels near the control level (FIG. 12). This indicates that SP and HK-1 are unlikely agonists of GPR15-like.

Example 11

Pain Control Effects of GPR83 Knockdown in Spinal Cord Cells by Intrathecal Administration of GPR83 siRNA 1. Purpose of Experiment In this experiment, the effects of intrathecal administration of GPR83 siRNA to suppress pain behavior following intraplantar administration of formalin were confirmed under GPR83 knockdown conditions.

2. Experimental Method and Results 4.5 mM (45 pmol/10 μl) GPR83 siRNA, 4.5 mM (45 pmol/10 μl) NK1R siRNA as target groups, 4.5 mM (45 pmol/10 μl) mismatch siRNA (MM siRNA: negative control), and 10 μl of HVJ-E (reagent for introduction of siRNA) were administered to intrathecally catheterized rats via catheters. On day 4 after administration, 50 μl of 2% formalin was administered subcutaneously to the hind paws of rats. The number of flinching events (pain behavior) was determined for a 60-minute period after formalin administration, so that the degree of pain was evaluated. During the 10-minute period after formalin administration (referred to as phase I), pain behavior was determined once every 2 minutes (1 minute per determination). During the period from 10 minutes to 60 minutes after formalin administration (referred to as phase II), pain behavior was determined once every 5 minutes (1 minute per determination), so that the degree of pain was evaluated. During phase I, behavior (phasic pain) resulting from chemical stimulation accompanying formalin administration was observed. During phase II, tonic pain following the phasic pain was observed.

Figure 13:
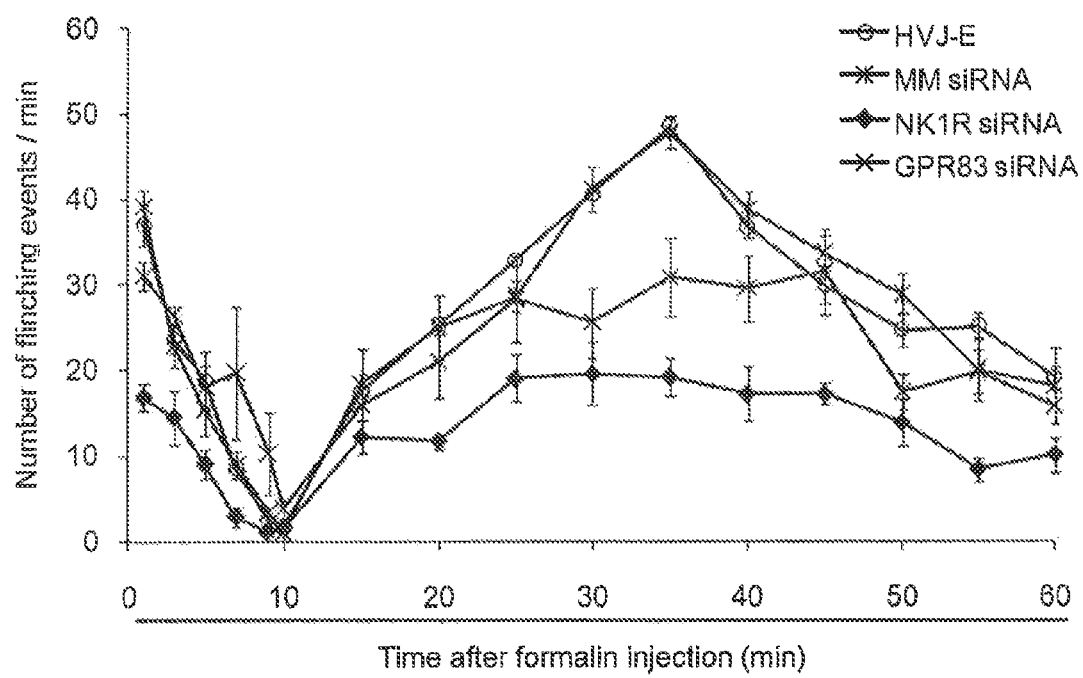
FIG. 13 shows the effects of suppressing formalin-induced pain by GPR83 siRNA.
Figure 14:
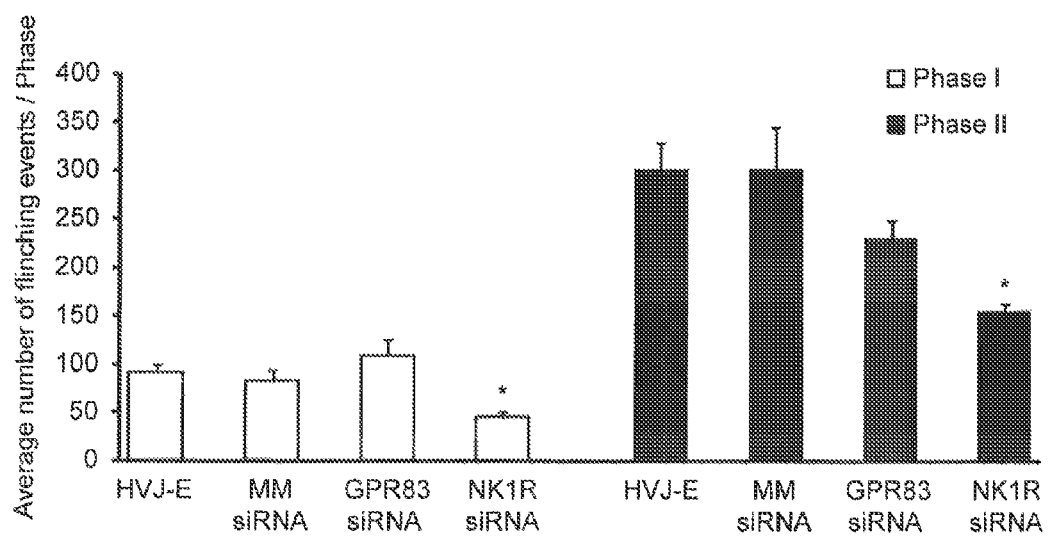
FIG. 14 shows the effects of suppressing formalin-induced pain by GPR83 siRNA.

FIG. 13 shows the results. The horizontal axis indicates time (minutes) after formalin administration and the vertical axis indicates the determined number of pain behavior events per minute. FIG. 14 shows the average numbers of pain behavior events determined during phase I and phase II.

As a result, in phase I, the group to which GPR83 siRNA had been administered showed no difference, in the number of pain behavior events compared with the group to which HVJ-E had been administered and the group to which MM siRNA had been administered. However, in the group to which NK1R siRNA had been administered, there were fewer pain behavior events. Meanwhile, in phase II, there were fewer pain behavior events in the group to which GPR83 siRNA had been administered, compared with the group to which HVJ-E had been administered and the group to which MM siRNA had been administered, but no significant difference was observed. The effect of suppressing pain behavior was observed in the group to which NK1R siRNA had been administered, compared with the group to which HVJ-E had been administered and the group to which MM siRNA had been administered. It was suggested by these results that in spinal cord cells, involvement of GPR83 in the pain transduction system was at a level lower than that of NK1R.

Example 12

Effects of GPR83 Knockdown in Spinal Cord Cells by the Intrathecal Administration of GPR83 siRNA to Suppress Itching Following Administration of Itching Inducer 1. Purpose of Experiment As in the results of FIG. 11, intrathecal administration of GPR83 siRNA under conditions of spinal cord cells with GPR83 knockdown could not suppress scratching behavior induced by intrathecal SP administration but could suppress HK-1-induced scratching behavior.

Meanwhile, as in the results of FIG. 13 and FIG. 14, in the group to which GPR83 siRNA had been administered, pain behavior resulting from subcutaneous administration of formalin could not be suppressed. Hence, to evaluate the physiological functions of GPR83 in the spinal cord, involvement in an itching transduction mechanism was examined. Specifically, to evaluate whether or not GPR83 is involved in itching resulting from administration of an itching inducer to the peripheral tissue, histamine and serotonin (5-HT), which are known as endogenous itching inducers, were separately administered to subcutaneous tissue in the nape of the neck of rats, and evaluation was performed using as an indicator whether or not changes in itching behavior occurred following administration of these itching inducers.

2. Experimental Method and Results 4.5 mM (45 pmol/10 μl) GPR83 siRNA, 4.5 mM (45 pmol/10 μl) NK1R siRNA as target groups, and 10 μl of HVJ-E (reagent for introduction of siRNA) were administered to intrathecally catheterized rats via catheters. On day 4 after administration, itching inducers ($10^{-3}$ M histamine (0.25 mg/50 μl) and $1.13 \times 10^{-4}$ M 5-HT (0.25 mg/50 μl)) were each subcutaneously administered to the nape of the neck, itching behavior was determined for a 20-minute period after administration, and thus the degree of itching was evaluated.

Figure 15:
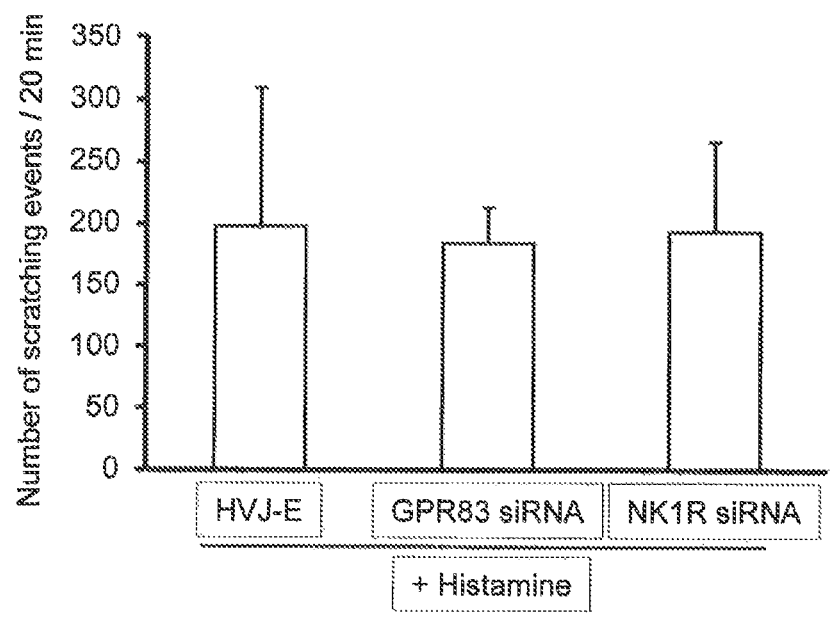
FIG. 15 shows the effects of suppressing histamine-induced pruritus by GPR83 siRNA.
Figure 16:
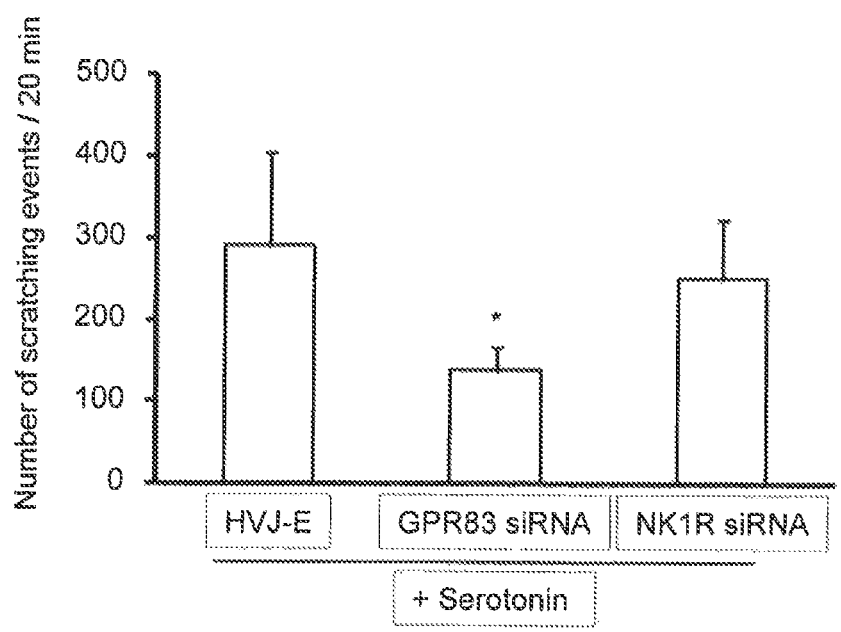
FIG. 16 shows the effects of suppressing serotonin-induced pruritus by GPR83 siRNA.

FIG. 15 and FIG. 16 show the results of observing itching behavior resulting from histamine administration and 5-HT administration. The vertical axis indicates the number of scratching events during a 20-minute period after administration of histamine and 5-HT, and the horizontal axis indicates HVJ-E (reagent for introduction of siRNA), GPR83 siRNA, and NK1R siRNA administered.

In FIG. 15, both the group to which GPR83 siRNA had been administered and the group to which NK1R siRNA had been administered exhibited itching behavior (resulting from histamine administration) at the same level as that of HVJ-E (control level). When the expression of these receptors was suppressed, no effect of suppressing itching behavior was observed.

Meanwhile, in FIG. 16, itching behavior resulting from 5-HT administration was observed to be suppressed in the group to which GPR83 siRNA had been administered, compared with the group to which HVJ-E had been administered. However, no difference was observed between the group to which NK1R siRNA had been administered and the group to which HVJ-E had been administered.

As described above, intrathecal administration of GPR83 siRNA could suppress itching behavior induced by subcutaneous administration of 5-HT. It was thus suggested that GPR83 expressed in spinal cord cells is involved in the 5-HT-induced itching transduction mechanism of peripheral tissue.

[Conclusion]

Taken together, after administration of HVJ-E into which siRNA targeting 3 types of gene had been introduced, scratching behavior resulting from SP administration or HK-1 administration gave rise to contrasting experimental results. Actually, scratching behavior resulting from SP administration was suppressed by NK1R siRNA pre-administration, and scratching behavior resulting from HK-1 administration was suppressed by GPR83 siRNA pre-administration.

Meanwhile, GPR15-like siRNA was not able to suppress any scratching behavior resulting from both SP administration and HK-1 administration. These results indicate that GPR83 is increasingly likely to be an HK-1 specific receptor. It could also be confirmed by a similar evaluation method that SP is an agonist of NK1R.

All publications, patents, and patent applications cited in this description are herein incorporated by reference in their entirety.

[Sequence Listing Free Text]

SEQ ID NO: 1: amidation.
SEQ ID NO: 2: amidation.
SEQ ID NO: 3: synthetic peptide. Amidation.
SEQ ID NO: 4: synthetic peptide. Amidation.
SEQ ID NO: 5: synthetic peptide. Amidation.
SEQ ID NO: 6: synthetic peptide. Amidation.
SEQ ID NO: 7: synthetic peptide. Amidation.
SEQ ID NO: 8: synthetic peptide. Xaa is D-tryptophan. Amidation.
SEQ ID NO: 9: synthetic peptide. Xaa is D-tryptophan. Amidation.
SEQ ID NO: 10: synthetic peptide. Amidation.
SEQ ID NO: 11: synthetic peptide. Amidation.
SEQ ID NO: 12: synthetic peptide. Amidation.
SEQ ID NO: 13: synthetic peptide. Amidation.
SEQ ID NO: 14: synthetic peptide. Amidation.
SEQ ID NO: 15: synthetic peptide. Amidation.
SEQ ID NO: 16: synthetic peptide. Amidation.

Sequence Listing

The Sequence Listing associated with this application is filed in electronic format via EFS-Web and hereby is incorporated by reference into the specification in its entirety. The name of the text file containing the Sequence Listing is Sequence_Listing_for_Divisional.txt. The size of the text file is 22 KB, and the text file was created on Aug. 5, 2015.

The invention claimed is:

1. A method for evaluating, in vivo, a test substance in a non-human animal, comprising:
   administering a GPR83 inhibitor to a first non-human animal and a second non-human animal, wherein the GPR83 inhibitor is selected from the group consisting of a polypeptide, an antibody, an antisense inhibitor, and an siRNA;
   administering a first test substance to the first non-human animal;
   administering a control substance to the second non-human animal;
   comparing itching behavior in the first non-human animal and itching behavior in the second non-human animal; and
   evaluating whether or not the first test substance is a pruritus-related substance based on an increase or decrease in itching behavior.

2. The method of claim 1, further comprising:
   determining that the first test substance is a pruritus inhibiting substance if the itching behavior in the first non-human animal is suppressed.

3. A method for evaluating, in vivo, a test substance in a non-human animal, comprising:
   administering a GPR83 inhibitor to a first non-human animal wherein the GPR83 inhibitor is selected from the group consisting of a polypeptide, an antibody, an antisense inhibitor, and an siRNA;
   administering a test substance to the first non-human animal;
   administering the test substance to a second non-human animal in which the GPR83 function is not inhibited;
   administering a compound that induces itching to the first non-human animal and the second non-human animal; and
   comparing itching behavior in the first non-human animal and itching behavior in the second non-human animal;
   wherein a decrease in the itching behavior in the first non-human animal compared to the second non-human animal indicates that the test substance is an agonist of GPR83, and
   wherein an increase in the itching behavior in the first non-human animal compared to the second non-human animal indicates that the test substance is an antagonist of GPR83.

4. The method of claim 3, wherein the compound that induces itching is selected from the group consisting of histamine and serotonin.

* * * * *

SEQUENCE LISTING

```
<160> NUMBER OF SEQ ID NOS: 44

<210> SEQ ID NO 1
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: AMIDATION

<400> SEQUENCE: 1

Arg Pro Lys Pro Gln Gln Phe Phe Gly Leu Met
1               5                   10

<210> SEQ ID NO 2
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: AMIDATION

<400> SEQUENCE: 2

Arg Ser Arg Thr Arg Gln Phe Tyr Gly Leu Met
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: AMIDATION
```

```
<400> SEQUENCE: 3

Arg Pro Lys Pro Gln Gln Phe
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 4

Phe Phe Gly Leu Met
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: AMIDATION

<400> SEQUENCE: 5

Arg Pro Lys Pro Gln Gln Phe Phe
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 6

Arg Pro Lys Pro Gln
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 7

Arg Ser Arg Thr Arg
1               5

<210> SEQ ID NO 8
<211> LENGTH: 5
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is the D-form of tryptophan
<220> FEATURE:
<221> NAME/KEY: MOD_RES
<222> LOCATION: (5)..(5)
<223> OTHER INFORMATION: AMIDATION

<400> SEQUENCE: 8

Arg Xaa Lys Pro Gln
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is the D-form of tryptophan
<220> FEATURE:
<221> NAME/KEY: MOD_RES
<222> LOCATION: (5)..(5)
<223> OTHER INFORMATION: AMIDATION

<400> SEQUENCE: 9

Arg Xaa Arg Thr Arg
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 10

Gln Phe Tyr Gly Leu Met
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: AMIDATION

<400> SEQUENCE: 11

Gln Phe Phe Gly Leu Met
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (5)..(5)
<223> OTHER INFORMATION: AMIDATION

<400> SEQUENCE: 12

Leu Pro Lys Pro Gln
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 13

Arg Pro Leu Pro Gln
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 14

Leu Ser Arg Thr Arg
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 15

Arg Ser Leu Thr Arg
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: AMIDATION

<400> SEQUENCE: 16

Arg Ser Arg Thr Leu
1               5
```

<210> SEQ ID NO 17
<211> LENGTH: 423
<212> TYPE: PRT
<213> ORGANISM: Homo sapiens

<400> SEQUENCE: 17

```
Met Val Pro His Leu Leu Leu Cys Leu Leu Pro Leu Val Arg Ala
1               5                   10                  15

Thr Glu Pro His Glu Gly Arg Ala Asp Glu Gln Ser Ala Glu Ala Ala
            20                  25                  30

Leu Ala Val Pro Asn Ala Ser His Phe Phe Ser Trp Asn Asn Tyr Thr
        35                  40                  45

Phe Ser Asp Trp Gln Asn Phe Val Gly Arg Arg Tyr Gly Ala Glu
50                  55                  60

Ser Gln Asn Pro Thr Val Lys Ala Leu Leu Ile Val Ala Tyr Ser Phe
65                  70                  75                  80

Ile Ile Val Phe Ser Leu Phe Gly Asn Val Leu Val Cys His Val Ile
                85                  90                  95

Phe Lys Asn Gln Arg Met His Ser Ala Thr Ser Leu Phe Ile Val Asn
            100                 105                 110

Leu Ala Val Ala Asp Ile Met Ile Thr Leu Leu Asn Thr Pro Phe Thr
        115                 120                 125

Leu Val Arg Phe Val Asn Ser Thr Trp Ile Phe Gly Lys Gly Met Cys
130                 135                 140

His Val Ser Arg Phe Ala Gln Tyr Cys Ser Leu His Val Ser Ala Leu
145                 150                 155                 160

Thr Leu Thr Ala Ile Ala Val Asp Arg His Gln Val Ile Met His Pro
                165                 170                 175

Leu Lys Pro Arg Ile Ser Ile Thr Lys Gly Val Ile Tyr Ile Ala Val
            180                 185                 190

Ile Trp Thr Met Ala Thr Phe Phe Ser Leu Pro His Ala Ile Cys Gln
        195                 200                 205

Lys Leu Phe Thr Phe Lys Tyr Ser Glu Asp Ile Val Arg Ser Leu Cys
210                 215                 220

Leu Pro Asp Phe Pro Glu Pro Ala Asp Leu Phe Trp Lys Tyr Leu Asp
225                 230                 235                 240

Leu Ala Thr Phe Ile Leu Leu Tyr Ile Leu Pro Leu Leu Ile Ile Ser
                245                 250                 255

Val Ala Tyr Ala Arg Val Ala Lys Lys Leu Trp Leu Cys Asn Met Ile
            260                 265                 270

Gly Asp Val Thr Thr Glu Gln Tyr Phe Ala Leu Arg Arg Lys Lys Lys
        275                 280                 285

Lys Thr Ile Lys Met Leu Met Leu Val Val Val Leu Phe Ala Leu Cys
290                 295                 300

Trp Phe Pro Leu Asn Cys Tyr Val Leu Leu Leu Ser Ser Lys Val Ile
305                 310                 315                 320

Arg Thr Asn Asn Ala Leu Tyr Phe Ala Phe His Trp Phe Ala Met Ser
                325                 330                 335

Ser Thr Cys Tyr Asn Pro Phe Ile Tyr Cys Trp Leu Asn Glu Asn Phe
            340                 345                 350

Arg Ile Glu Leu Lys Ala Leu Leu Ser Met Cys Gln Arg Pro Pro Lys
        355                 360                 365

Pro Gln Glu Asp Arg Pro Pro Ser Pro Val Pro Ser Phe Arg Val Ala
370                 375                 380
```

```
Trp Thr Glu Lys Asn Asp Gly Gln Arg Ala Pro Leu Ala Asn Asn Leu
385                 390                 395                 400

Leu Pro Thr Ser Gln Leu Gln Ser Gly Lys Thr Asp Leu Ser Ser Val
            405                 410                 415

Glu Pro Ile Val Thr Met Ser
            420

<210> SEQ ID NO 18
<211> LENGTH: 423
<212> TYPE: PRT
<213> ORGANISM: Mus musculus

<400> SEQUENCE: 18

Met Lys Val Pro Pro Val Leu Leu Phe Leu Leu Ser Ser Val Arg
1               5                   10                  15

Ala Thr Glu Gln Pro Gln Val Val Thr Glu His Pro Ser Met Glu Ala
                20                  25                  30

Ala Leu Thr Gly Pro Asn Ala Ser Ser His Phe Trp Ala Asn Tyr Thr
            35                  40                  45

Phe Ser Asp Trp Gln Asn Phe Val Gly Arg Arg Tyr Gly Ala Glu
    50                  55                  60

Ser Gln Asn Pro Thr Val Lys Ala Leu Leu Ile Val Ala Tyr Ser Phe
65                  70                  75                  80

Thr Ile Val Phe Ser Leu Phe Gly Asn Val Leu Val Cys His Val Ile
                85                  90                  95

Phe Lys Asn Gln Arg Met His Ser Ala Thr Ser Leu Phe Ile Val Asn
                100                 105                 110

Leu Ala Val Ala Asp Ile Met Ile Thr Leu Leu Asn Thr Pro Phe Thr
            115                 120                 125

Leu Val Arg Phe Val Asn Ser Thr Trp Val Phe Gly Lys Gly Met Cys
        130                 135                 140

His Val Ser Arg Phe Ala Gln Tyr Cys Ser Leu His Val Ser Ala Leu
145                 150                 155                 160

Thr Leu Thr Ala Ile Ala Val Asp Arg His Gln Val Ile Met His Pro
                165                 170                 175

Leu Lys Pro Arg Ile Ser Ile Thr Lys Gly Val Ile Tyr Ile Ala Val
            180                 185                 190

Ile Trp Val Met Ala Thr Phe Phe Ser Leu Pro His Ala Ile Cys Gln
        195                 200                 205

Lys Leu Phe Thr Phe Lys Tyr Ser Glu Asp Ile Val Arg Ser Leu Cys
210                 215                 220

Leu Pro Asp Phe Pro Glu Pro Ala Asp Leu Phe Trp Lys Tyr Leu Asp
225                 230                 235                 240

Leu Ala Thr Phe Ile Leu Leu Tyr Leu Leu Pro Leu Phe Ile Ile Ser
                245                 250                 255

Val Ala Tyr Ala Arg Val Ala Lys Lys Leu Trp Leu Cys Asn Thr Ile
            260                 265                 270

Gly Asp Val Thr Thr Glu Gln Tyr Leu Ala Leu Arg Arg Lys Lys Lys
        275                 280                 285

Thr Thr Val Lys Met Leu Val Leu Val Val Leu Phe Ala Leu Cys
290                 295                 300

Trp Phe Pro Leu Asn Cys Tyr Val Leu Leu Ser Ser Lys Ala Ile
305                 310                 315                 320

His Thr Asn Asn Ala Leu Tyr Phe Ala Phe His Trp Phe Ala Met Ser
                325                 330                 335
```

-continued

```
Ser Thr Cys Tyr Asn Pro Phe Ile Tyr Cys Trp Leu Asn Glu Asn Phe
            340                 345                 350

Arg Val Glu Leu Lys Ala Leu Leu Ser Met Cys Gln Arg Pro Pro Lys
            355                 360                 365

Pro Gln Glu Asp Arg Leu Pro Ser Pro Val Pro Ser Phe Arg Val Ala
            370                 375                 380

Trp Thr Glu Lys Ser His Gly Arg Arg Ala Pro Leu Pro Asn His His
385                 390                 395                 400

Leu Pro Ser Ser Gln Ile Gln Ser Gly Lys Thr Asp Leu Ser Ser Val
            405                 410                 415

Glu Pro Val Val Ala Met Ser
            420

<210> SEQ ID NO 19
<211> LENGTH: 422
<212> TYPE: PRT
<213> ORGANISM: Canis lupus familiaris

<400> SEQUENCE: 19

Met Gly Arg Arg Gly Ala Leu Leu Cys Leu Leu Pro Leu Leu Arg Ala
1               5                   10                  15

Ala Glu Arg Pro Glu Gly Arg Ala Asp Glu Pro Gly Leu Glu Ala Ala
            20                  25                  30

Leu Ala Gly Pro Asn Ala Ser His Phe Phe Trp Ser Asn Tyr Ser Phe
            35                  40                  45

Ser Asp Trp Gln Asn Phe Val Gly Arg Arg Tyr Gly Ala Glu Ser
        50                  55                  60

Gln Asn Pro Thr Val Lys Ala Leu Leu Val Val Ala Tyr Ser Phe Ile
65                  70                  75                  80

Ile Val Phe Ser Leu Phe Gly Asn Val Leu Val Cys His Val Ile Phe
                85                  90                  95

Lys Asn Gln Arg Met Arg Ser Ala Thr Ser Leu Phe Ile Val Asn Leu
            100                 105                 110

Ala Val Ala Asp Ile Leu Ile Thr Leu Leu Asn Thr Pro Phe Thr Leu
            115                 120                 125

Val Arg Phe Val Asn Ser Thr Trp Val Phe Gly Lys Gly Met Cys His
            130                 135                 140

Val Ser Arg Phe Ala Gln Tyr Cys Ser Leu His Val Ser Ala Leu Thr
145                 150                 155                 160

Leu Thr Ala Ile Ala Val Asp Arg His Gln Val Ile Met His Pro Leu
            165                 170                 175

Lys Pro Arg Ile Ser Ile Thr Lys Gly Val Ile Tyr Ile Thr Val Ile
            180                 185                 190

Trp Thr Met Ala Thr Phe Phe Ser Leu Pro His Ala Ile Cys Gln Lys
            195                 200                 205

Leu Phe Thr Phe Lys Tyr Ser Glu Asp Ile Val Arg Ser Leu Cys Leu
            210                 215                 220

Pro Asp Phe Pro Glu Pro Ala Asp Leu Phe Trp Lys Tyr Leu Asp Leu
225                 230                 235                 240

Ala Thr Phe Ile Leu Leu Tyr Ile Leu Pro Leu Leu Ile Ile Ser Val
            245                 250                 255

Ala Tyr Ala Arg Val Ala Lys Lys Leu Trp Leu Cys Asn Thr Ile Gly
            260                 265                 270

Asp Val Thr Thr Glu Gln Tyr Leu Ala Leu Arg Arg Lys Lys Lys Lys
            275                 280                 285
```

```
Thr Ile Lys Met Leu Met Leu Val Val Leu Phe Ala Leu Cys Trp
        290                 295                 300
Phe Pro Leu Asn Cys Tyr Val Leu Leu Ser Ser Lys Val Ile His
305                 310                 315                 320
Thr Asn Asn Ala Leu Tyr Phe Ala Phe His Trp Phe Ala Met Ser Ser
                325                 330                 335
Thr Cys Tyr Asn Pro Phe Ile Tyr Cys Trp Leu Asn Glu Asn Phe Arg
                340                 345                 350
Ile Glu Leu Lys Ala Leu Leu Ser Met Cys Gln Arg Leu Pro Lys Pro
            355                 360                 365
Gln Glu Glu Arg Pro Pro Ser Pro Val Pro Ser Phe Arg Val Ala Trp
370                 375                 380
Thr Glu Lys Ser Asn Gly Arg Arg Val Pro Pro Ala Asn Asn Leu Leu
385                 390                 395                 400
Leu Ser Ser His Leu His Ser Gly Lys Thr Asp Leu Ser Ser Val Glu
                405                 410                 415
Pro Ile Val Ala Met Ser
            420

<210> SEQ ID NO 20
<211> LENGTH: 415
<212> TYPE: PRT
<213> ORGANISM: Bos taurus

<400> SEQUENCE: 20

Met Thr Pro Gly Trp Val Leu Leu Cys Leu Leu Pro Ala Val Arg Ala
1               5                   10                  15
Ala Asp Glu Arg Ser Pro Gly Ala Ala Leu Ala Gly Pro Asn Ala Ser
                20                  25                  30
His Phe Phe Trp Asn Asn Tyr Thr Phe Ser Asp Trp Gln Asn Phe Val
            35                  40                  45
Gly Arg Arg Arg Tyr Gly Ala Glu Ser Gln Asn Pro Thr Val Lys Ala
        50                  55                  60
Leu Leu Ile Val Ala Tyr Ser Phe Ile Ile Phe Ser Leu Phe Gly
65                  70                  75                  80
Asn Val Leu Val Cys His Val Ile Phe Lys Asn Gln Arg Met His Ser
                85                  90                  95
Ala Thr Ser Leu Phe Ile Val Asn Leu Ala Val Ala Asp Ile Met Ile
                100                 105                 110
Thr Leu Leu Asn Thr Pro Phe Thr Leu Val Arg Phe Val Asn Ser Thr
            115                 120                 125
Trp Val Phe Gly Lys Gly Met Cys His Ile Ser Arg Phe Ala Gln Tyr
        130                 135                 140
Cys Ser Leu His Val Ser Ala Leu Thr Leu Thr Ala Ile Ala Val Asp
145                 150                 155                 160
Arg His Gln Val Ile Met His Pro Leu Lys Pro Arg Ile Ser Ile Thr
                165                 170                 175
Lys Gly Val Ile Tyr Ile Ala Val Ile Trp Thr Met Ala Thr Phe Phe
            180                 185                 190
Ser Leu Pro His Ala Ile Cys Gln Lys Leu Phe Thr Phe Lys Tyr Ser
        195                 200                 205
Glu Asp Val Val Arg Ser Leu Cys Leu Pro Asp Phe Pro Glu Pro Ala
    210                 215                 220
Asp Leu Phe Trp Lys Tyr Leu Asp Leu Ala Thr Phe Ile Leu Leu Tyr
225                 230                 235                 240
```

-continued

```
Ile Leu Pro Leu Leu Ile Ser Val Ala Tyr Ala Arg Val Ala Lys
                245                 250                 255

Lys Leu Trp Leu Cys Asn Thr Ile Gly Asp Val Thr Thr Lys Gln Tyr
            260                 265                 270

Leu Ala Leu Arg Arg Lys Lys Lys Thr Ile Lys Met Leu Met Leu
        275                 280                 285

Val Val Val Leu Phe Ala Leu Cys Trp Phe Pro Leu Asn Cys Tyr Val
    290                 295                 300

Leu Leu Leu Ser Ser Lys Val Ile Arg Thr Asn Asn Ala Leu Tyr Phe
305                 310                 315                 320

Ala Phe His Trp Phe Ala Met Ser Ser Thr Cys Tyr Asn Pro Phe Ile
                325                 330                 335

Tyr Cys Trp Leu Asn Glu Asn Phe Arg Val Glu Leu Lys Ala Leu Leu
            340                 345                 350

His Met Cys Gln Arg Ser Pro Lys Pro Gln Glu Gly Gln Pro Pro Ser
        355                 360                 365

Pro Val Pro Ser Leu Arg Val Ala Trp Ala Glu Lys Ser Ser Gly Arg
    370                 375                 380

Arg Ala Ser Pro Ala Asn Ser Leu Leu Pro Ser Ser Gln Val Gln Ser
385                 390                 395                 400

Gly Arg Thr Asp Leu Ala Ser Val Glu Pro Ile Val Thr Met Thr
                405                 410                 415

<210> SEQ ID NO 21
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 21
caacaggacu uaugagaaat t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 22
uuucucauaa guccuguugt t                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 23
caucagugca ggugauuaut t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic RNA and DNA sequence
```

<400> SEQUENCE: 24
auaaucaccu gcacugaugt t                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 25
gcagagaacu ucacaggaat t                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 26
uuccugugaa guucucugct t                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 27
auccgcgcga uaguacguat t                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 28
uacguacuau cgcgcggaut t                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 29
uuacgcguag cguaauacgt t                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 30
cguauuacgc uacgcguaat t                                              21

```
<210> SEQ ID NO 31
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 31
uauucgcgcg uauagcggut t                                            21

<210> SEQ ID NO 32
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 32
accgcuauac gcgcgaauat t                                            21

<210> SEQ ID NO 33
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 33
gcacaugggu guuugggaat t                                            21

<210> SEQ ID NO 34
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 34
uucccaaaca cccaugugct t                                            21

<210> SEQ ID NO 35
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 35 ccacugugc cgugaguuat t                                             21

<210> SEQ ID NO 36
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 36
uaacucacgg ccacaguggt t                                            21

<210> SEQ ID NO 37
<211> LENGTH: 21
<212> TYPE: DNA
<213> ORGANISM: Artificial Sequence
<220> FEATURE:
<223> OTHER INFORMATION: Synthetic RNA and DNA sequence
```

```
<400> SEQUENCE: 37
gggaggagcu ucagccauat t                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 38
uauggcugaa gcuccuccct t                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 39
gaucaaagcu gcaaucauat t                                              21

<210> SEQ ID NO 40
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 40
uaugauugca gcuuugauct t                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 41
ccaaugaaac caaggcuaat t                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 42
uuagccuugg uuucauuggt t                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 43
ggacauuuau cuugcuguat t                                              21
```

-continued

```
<210> SEQ ID NO 44
<211> LENGTH: 21
<212> TYPE: DNA
<213> ORGANISM: Artificial Sequence
<220> FEATURE:
<223> OTHER INFORMATION: Synthetic RNA and DNA sequence

<400> SEQUENCE: 44
uacagcaaga uaaaugucct t                                              21
```